US010321926B2

(12) United States Patent
McCulloch et al.

(10) Patent No.: US 10,321,926 B2
(45) Date of Patent: *Jun. 18, 2019

(54) DEVICES AND METHODS FOR ANTERIOR ARYTENOID ADDUCTION

(71) Applicants: Timothy M. McCulloch, Madison, WI (US); Matthew R. Hoffman, Dousman, WI (US)

(72) Inventors: Timothy M. McCulloch, Madison, WI (US); Matthew R. Hoffman, Dousman, WI (US)

(*) Notice: Subject to any disclaimer, the term of this patent is extended or adjusted under 35 U.S.C. 154(b) by 505 days.

This patent is subject to a terminal disclaimer.

(21) Appl. No.: 15/008,916

(22) Filed: Jan. 28, 2016

(65) Prior Publication Data

US 2016/0183958 A1 Jun. 30, 2016

Related U.S. Application Data

(63) Continuation of application No. 13/834,623, filed on Mar. 15, 2013, now Pat. No. 9,277,913.

(Continued)

(51) Int. Cl.
A61B 17/04 (2006.01)
A61B 17/24 (2006.01)
(Continued)

(52) U.S. Cl.
CPC .......... A61B 17/24 (2013.01); A61B 17/0057 (2013.01); A61B 17/0401 (2013.01);
(Continued)

(58) Field of Classification Search
CPC . A61B 17/0057; A61B 17/0401; A61B 17/06; A61B 17/06004; A61B 17/24;
(Continued)

(56) References Cited

U.S. PATENT DOCUMENTS 5,197,982 A 3/1993 Goldsmith, III
5,242,457 A 9/1993 Akopov et al.
(Continued)

FOREIGN PATENT DOCUMENTS

WO 2008/040914 4/2008
WO 2013/158289 10/2013

OTHER PUBLICATIONS

PCT/US2013/032023 International Search Report and Written Opinion dated Jul. 29, 2013 (10 pages).
(Continued)

Primary Examiner — Ryan J. Severson
(74) Attorney, Agent, or Firm — Michael Best & Friedrich LLP

(57) ABSTRACT

Provided herein are devices and methods for anterior arytenoid adduction. The device may comprise a wire having a first end and a second end at opposite ends of a longitudinal axis, the wire forming a spiral along the longitudinal axis and having a double hook at the first end, a suture threaded through the spiral of the wire from the second end to the first end, the suture forming a turn at the first end and passing exterior to the spiral to the second end. The method may comprise advancing a suture and hook from the subject's anterior thyroid cartilage or cricothyroid membrane to the muscular process of the subject's arytenoid, attaching the hook to the muscular process, and applying tension to the suture to rotate the muscular process and adduct the arytenoid.

10 Claims, 26 Drawing Sheets

Related U.S. Application Data

(60) Provisional application No. 61/625,860, filed on Apr. 18, 2012.

(51) Int. Cl.
| | |
|---|---|
| *A61M 29/02* | (2006.01) |
| *A61M 5/00* | (2006.01) |
| *A61B 90/00* | (2016.01) |
| *A61B 17/00* | (2006.01) |
| *A61F 2/40* | (2006.01) |
| *A61F 2/20* | (2006.01) |
| *A61B 17/34* | (2006.01) |

(52) U.S. Cl.
CPC ............. *A61B 90/06* (2016.02); *A61F 2/20* (2013.01); *A61F 2/40* (2013.01); *A61M 5/00* (2013.01); *A61M 29/02* (2013.01); *A61B 17/0487* (2013.01); *A61B 17/3421* (2013.01); *A61B 2017/0409* (2013.01); *A61B 2017/0414* (2013.01); *A61B 2017/0437* (2013.01); *A61B 2017/0496* (2013.01); *A61B 2090/063* (2016.02); *A61B 2090/3614* (2016.02)

(58) Field of Classification Search
CPC A61B 2017/00575; A61B 2017/00623; A61B 2017/00646; A61B 2017/00663; A61B 2017/0409; A61B 2017/0496; A61B 2017/0498; A61B 2017/06028; A61B 2017/06052; A61B 2017/06076; A61B 2017/061; A61B 2017/06171
See application file for complete search history.

(56) References Cited

U.S. PATENT DOCUMENTS

| | | | |
|---|---|---|---|
| 5,306,298 A | 4/1994 | Godley, III | |
| 5,344,453 A | 9/1994 | Montgomery | |
| 5,368,601 A | 11/1994 | Sauer et al. | |
| 5,372,604 A | 12/1994 | Trott | |
| 5,478,353 A * | 12/1995 | Yoon | A61B 17/0057 606/104 |
| 5,855,607 A | 1/1999 | Friedrich | |
| 5,972,024 A * | 10/1999 | Northrup, III | A61B 17/06166 606/151 |
| 7,917,220 B2 | 3/2011 | Muller | |
| 8,123,768 B2 * | 2/2012 | Vardi | A61B 17/00234 606/139 |
| 8,136,532 B2 | 3/2012 | Lindenthaler | |
| 8,337,388 B2 * | 12/2012 | Vardi | A61B 17/00234 600/37 |
| 8,380,313 B2 | 2/2013 | Muller | |
| 8,430,860 B2 | 4/2013 | Lindenthaler | |
| 8,460,270 B2 | 6/2013 | Muller | |
| 8,613,767 B2 | 12/2013 | Hoffman | |
| 8,788,036 B2 | 7/2014 | Lindenthaler | |
| 9,046,005 B2 | 6/2015 | Hoffman | |
| 9,056,005 B2 * | 6/2015 | Hoffman | A61F 2/20 |
| 9,277,913 B2 * | 3/2016 | McCulloch | A61B 17/0401 |
| 9,675,341 B2 * | 6/2017 | D'Agostino | A61B 17/06166 |
| 2004/0034387 A1 * | 2/2004 | Newman | A61B 17/0057 606/213 |
| 2005/0075654 A1 * | 4/2005 | Kelleher | A61B 17/0401 606/151 |
| 2006/0228391 A1 * | 10/2006 | Seyedin | A61K 31/727 424/422 |
| 2007/0093861 A1 * | 4/2007 | Vardi | A61B 17/00234 606/153 |
| 2007/0203511 A1 * | 8/2007 | Vardi | A61B 17/00234 606/153 |
| 2008/0071230 A1 | 3/2008 | Lindenthaler | |
| 2008/0071231 A1 | 3/2008 | Lindenthaler | |
| 2008/0071244 A1 | 3/2008 | Lindenthaler | |
| 2008/0071245 A1 | 3/2008 | Muller | |
| 2008/0091247 A1 | 4/2008 | Muller | |
| 2008/0114378 A1 * | 5/2008 | Matsushita | A61B 17/0401 606/143 |
| 2008/0228030 A1 | 9/2008 | Godin | |
| 2009/0099595 A1 | 4/2009 | Cheng | |
| 2011/0178529 A1 | 7/2011 | Muller | |
| 2011/0301580 A1 | 12/2011 | Hoffman | |
| 2012/0065680 A1 | 3/2012 | Green et al. | |
| 2012/0150293 A1 | 6/2012 | Hoffman | |
| 2013/0226233 A1 * | 8/2013 | D'Agostino | A61B 17/04 606/228 |
| 2013/0245639 A1 | 9/2013 | Lindenthaler | |
| 2013/0281973 A1 | 10/2013 | McCulloch | |
| 2016/0183958 A1 * | 6/2016 | McCulloch | A61B 17/0401 623/14.11 |

OTHER PUBLICATIONS

Czerwonka et al., "A-P Positioning of Medialization Thyroplasty in an Excised Larynx Model," Laryngoscope 2009, 119, 591-6.

Hoffman et al., "Optimal Arytenoid Adduction Based on Quantitative Real-TimeVoice Analysis," Laryngoscope 2011, 121, 339-345.

Isshiki N, et al., "Arytenoid Adduction for Unilateral Vocal Cord Paralysis," Arch. Otolaryngol. 1978, 104, pp. 555-558.

Jiang et al., "A Methodological Study of Hemilaryngeal Phonation," Laryngoscope 1993, 103, 872-82.

* cited by examiner

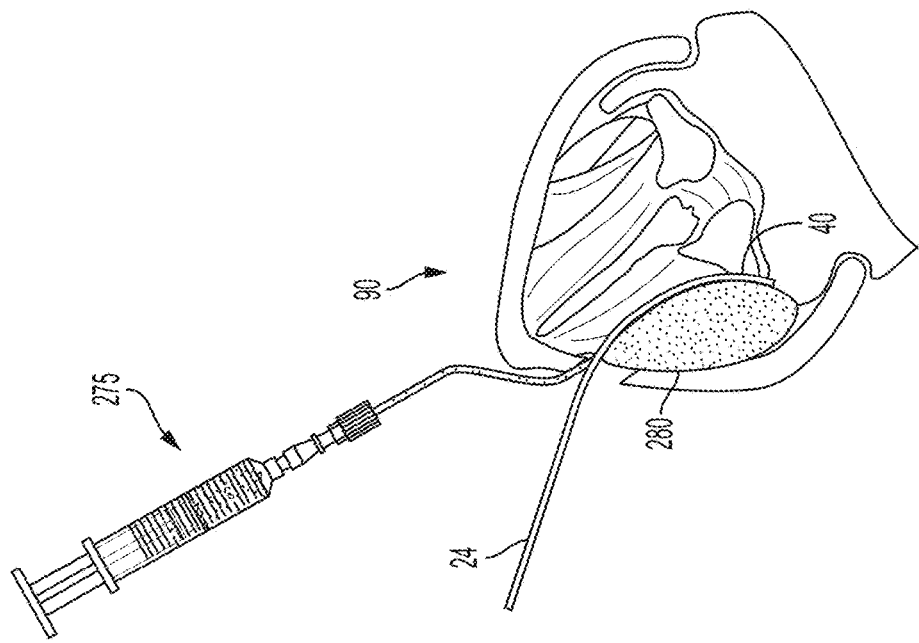
FIG. 24c
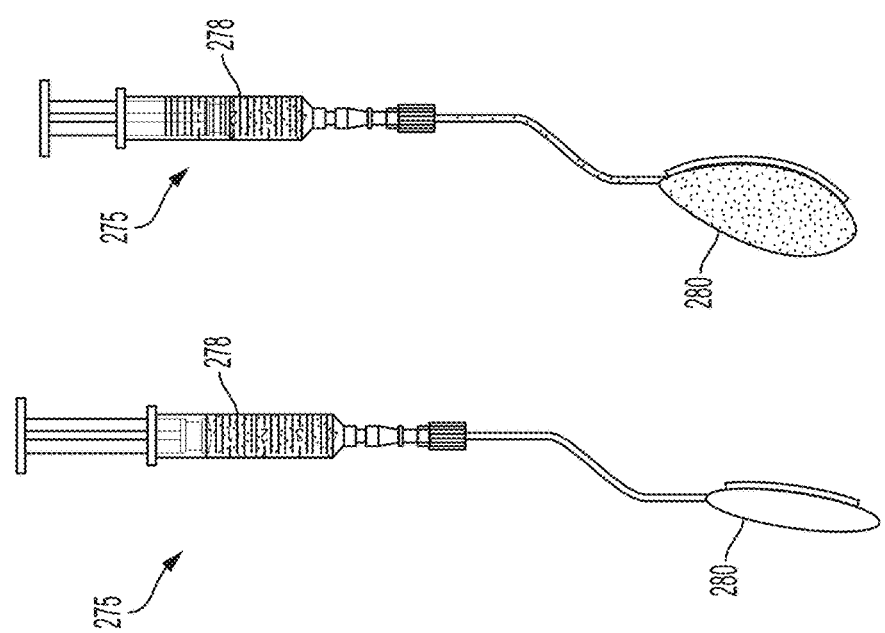
FIG. 24b
FIG. 24a

DEVICES AND METHODS FOR ANTERIOR ARYTENOID ADDUCTION

CROSS-REFERENCE TO RELATED APPLICATIONS

This application is a continuation of U.S. patent application Ser. No. 13/834,623, filed Mar. 15, 2013, which claims priority to U.S. Provisional Patent Application No. 61/625,860, filed Apr. 18, 2012. These applications are incorporated herein by reference in their entirety.

INTRODUCTION

The vocal folds, also known commonly as vocal cords, are two elastic bands of muscle tissue located in the larynx directly above the trachea. When you breathe, your vocal folds remain apart and when you swallow, they are tightly closed. When you use your voice, however, air from the lungs causes your vocal folds to vibrate between open and closed positions. Vocal fold paralysis ("VFP", also known as vocal cord paralysis) is a voice disorder that occurs when one or both of the vocal folds don't open or close properly. If you have vocal fold paralysis, the paralyzed fold or folds may remain open, leaving the air passages and lungs unprotected. You could have difficulty swallowing, and food or liquids could accidentally enter the trachea and lungs, causing serious health problems. Furthermore. VFP provides a voice that is weak and breathy and coughing and pulmonary function is impaired.

VFP is caused by injury to the recurrent laryngeal nerve (RLN), the nerve which innervates the intrinsic muscles of the larynx, its loss causes the vocal fold laterial displacement. Treatment is primarily surgical and aims to medialize the paralyzed fold. Current treatments include injection laryngoplasty, medialization thyroplasty with insertion of an implant, and arytenoid adduction. While injection laryngoplasty is a simple procedure which can be performed within the office, it cannot correct severe atrophy and lateralization caused by paralysis, cannot be reversed, and has an effect which wanes over time. Arytenoid adduction is a procedure that can correct very severe VFP and addresses vocal fold superoinferior asymmetry. Arytenoid adduction is procedure that is performed to rotate the position of the arytenoid and vocal fold. The vocal fold is tethered on the arytenoid cartilage. During an arytenoid adduction, the cartilage is repositioned to move the vocal fold to a position for optimal voice production. Furthermore, a modified arytenoid adduction can be used for any case of glottic insufficiency. Glottic insufficiency would also include such disorders as presbylaryngis, vocal fold scar, or muscular atrophy of the vocal fold.

While arytenoid adduction is a powerful procedure which can dramatically improve voice quality, it is technically challenging to perform. To perform arytenoid adduction, a large neck incision is made to access the larynx, the larynx is rotated, and sutures are passed from the posterior larynx (specifically, the muscular process of the arytenoid) anteriorly through the thyroid cartilage. It is difficult to access the posterior larynx. Doing so requires a highly invasive procedure; difficulty accessing the posterior larynx can also increase patient morbidity, particularly when done by surgeons inexperienced with the procedure.

SUMMARY

In one aspect, the invention provides a device for arytenoid adduction. The device comprises a wire hook complex with a suture connected to the hook to form a suture wire complex. In one embodiment of the suture wire complex, the complex comprises a wire hook complex, the wire hook complex comprising a wire having a first end and a second end at opposite ends of a longitudinal axis, the wire forming a spiral along a longitudinal axis and having a hook at the first end. A suture is threaded through the spiral of the wire from the second end to the first end of the wire, the suture forming a turn at the first end and passing exterior to the spiral to the second end of the wire, forming the suture wire complex. In other embodiments of the suture wire complex, the suture is connected to the wire through other conventional means. The device further comprises a first needle enclosing the suture wire complex. The device may further comprise a second needle enclosed by the first needle along with the suture wire complex. The device may further comprise a localizing trocar for enclosing the first needle.

In a further aspect, the invention provides a method for anterior arytenoid adduction in a subject in need thereof. The method comprises advancing the suture wire complex of the present invention through the subject's anterior thyroid cartilage or cricothyroid membrane to the muscular process of the subject's larynx, attaching the hook of the suture wire complex to the soft tissues surrounding the muscular process, and applying tension to the suture to rotate the muscular process and adduct the arytenoid.

Another aspect of the disclosure provides a method of adducting an arytenoid in a subject in need thereof. The method comprises providing a device comprising a first needle which encloses a suture wire complex. A guide needle can be used to locate the muscular process of the arytenoid through which the first needle is passed. The guide needle is passed through an incision in the subject's anterior thyroid cartilage or cricothyroid membrane to the muscular process of the subject's larynx. The first needle containing the suture wire complex is then passed through the guide needle. When the first needle reaches the muscular process, the suture wire complex is pushed outside the first needle and the suture wire complex is attached by the hook to the muscular process itself, and tension is applied to the suture to rotate the muscular process and adduct the arytenoid. In another embodiment, a second needle is provided that can be enclosed by the first needle, the second needle at least partially enclosing the suture wire complex. In other embodiments, optionally when the second needle is used, the first needle can act as the guide needle, and a separate guide needle is not needed.

In another embodiment of the invention, the device can also comprise a thyroplasty implant. In this embodiment the device comprises a wire hook with a suture connected to the hook to form a suture wire complex. In one specific embodiment, the suture wire complex comprises a wire having a first end and a second end at opposite ends of a longitudinal axis, the wire forming a spiral along the longitudinal axis and having a hook at the first end. A suture is threaded through the spiral of the wire from the second end to the first end of the wire, the suture forming a turn at the first end and passing exterior to the spiral to the second end of the wire to form the suture wire complex. The device further comprises a thyroplasty implant having a body with a central aperture, in which the suture is passed through the aperture of the implant. The device further comprises a first needle enclosing the suture wire complex and implant. The device may further comprise a guide needle through which the first needle will be passed. The device may also further comprise a second needle which can be enclosed by the first needle and at least partially enclose the suture wire complex. The device may further comprise a localizing trocar for enclosing the first needle and guide needle.

In another aspect of the present invention, a method of adducting an arytenoid and providing a thyroplasty implant is provided to a subject in need thereof. The method comprises providing a device comprising a first needle enclosing a suture wire complex. The device further comprises a thyroplasty implant having a body with a central aperture, in which the suture is passed through the aperture of the implant. A localizing trocar and first needle (or guide needle enclosing the first needle if used) are passed through the trocar. A second needle can be used and passed through the first needle, the second guide needle at least partially enclosing the suture wire complex. The first needle (or guide needle if used) is passed through an incision in the subject's anterior thyroid cartilage or cricothyroid membrane to the muscular process of the subject's arytenoid. The first needle containing the suture wire complex is then passed over the guide needle, if a guide needle is used. When the first needle reaches the muscular process, the suture wire complex is pushed outside the first needle and the suture wire complex is deployed and attached by the hook to the muscular process, and tension is applied to the suture to rotate the muscular process and adduct the arytenoid and medialize the vocal fold. The implant is then advanced along the suture and placed adjacent to the muscular process to aid in providing bulk to the vocal fold and closing the glottal gap.

In another aspect, provided are methods of delivering a composition to a vocal fold of a subject in need thereof. The method may include providing a suture wire complex comprising a wire hook connected to a suture, the wire hook complex comprising a wire having a first end and a second end at opposite ends of a longitudinal axis, the wire forming a spiral along the longitudinal axis and having a hook at the first end, and a suture threaded through the spiral of the wire from the second end to the first end, the suture forming a turn at the first end and passing exterior to the spiral to the second end; advancing the suture wire complex from the subject's anterior thyroid cartilage to the vocal fold; and advancing the composition from the subject's anterior thyroid cartilage to the vocal fold along the longitudinal axis of the wire hook complex. The composition may include at least one of a pharmaceutical compound, polypeptide, polynucleotide, cytokine, hormone, and stem cell. A first needle may enclose the suture wire complex, and the composition may be advanced along the longitudinal axis of a second needle enclosed by the first needle. A localizing trocar may enclose the first needle.

In another aspect, provided are methods of determining the volume of a glottal gap in the larynx of a subject. The method may include providing a suture wire complex comprising a wire hook complex connected to a suture, the wire hook complex comprising a wire having a first end and a second end at opposite ends of a longitudinal axis, the wire forming a spiral along the longitudinal axis and having a hook at the first end, and a suture threaded through the spiral of the wire from the second end to the first end, the suture forming a turn at the first end and passing exterior to the spiral to the second end; providing a volume measuring device comprising a syringe and a volume measuring balloon; advancing the suture wire complex from the subject's anterior thyroid cartilage to the muscular process of the subject's larynx; advancing the balloon along the longitudinal axis of the suture wire complex to the muscular process next to the glottal gap; inflating the balloon inside the thyroid cartilage to exert pressure on the subject's muscular process to reach a final volume necessary to medialize the vocal fold and close the glottal gap; determining the volume of the filled balloon using the calibrated syringe; and determining the volume necessary to medialize the vocal fold and close the glottal gap, wherein the volume necessary is equal to the volume of the filled balloon and measured by the calibrated syringe.

The disclosure provides for other aspects and embodiments that will be apparent in light of the following detailed description and accompanying Figures.

BRIEF DESCRIPTION OF THE DRAWINGS

FIG. 24a is a schematic diagram of a volume measuring device, with the balloon of the device in a deflated position.

FIG. 24b is a schematic diagram of a volume measuring device, with the balloon of the device in an inflated position.

FIG. 24c is a schematic superior view of the larynx, where an embodiment of the suture wire complex of the present invention has been connected to the muscular process and the balloon of the volume measuring device (shown in an inflated position) has been passed along one of the suture strands. The inflated balloon of the volume measuring device has been used to measure the volume required in the vocal fold to close the glottal gap.

DETAILED DESCRIPTION

A novel approach to arytenoid adduction (AA) is disclosed herein. Arytenoid adduction is a process used to help medialize the vocal folds of a patient.

Figure 1:
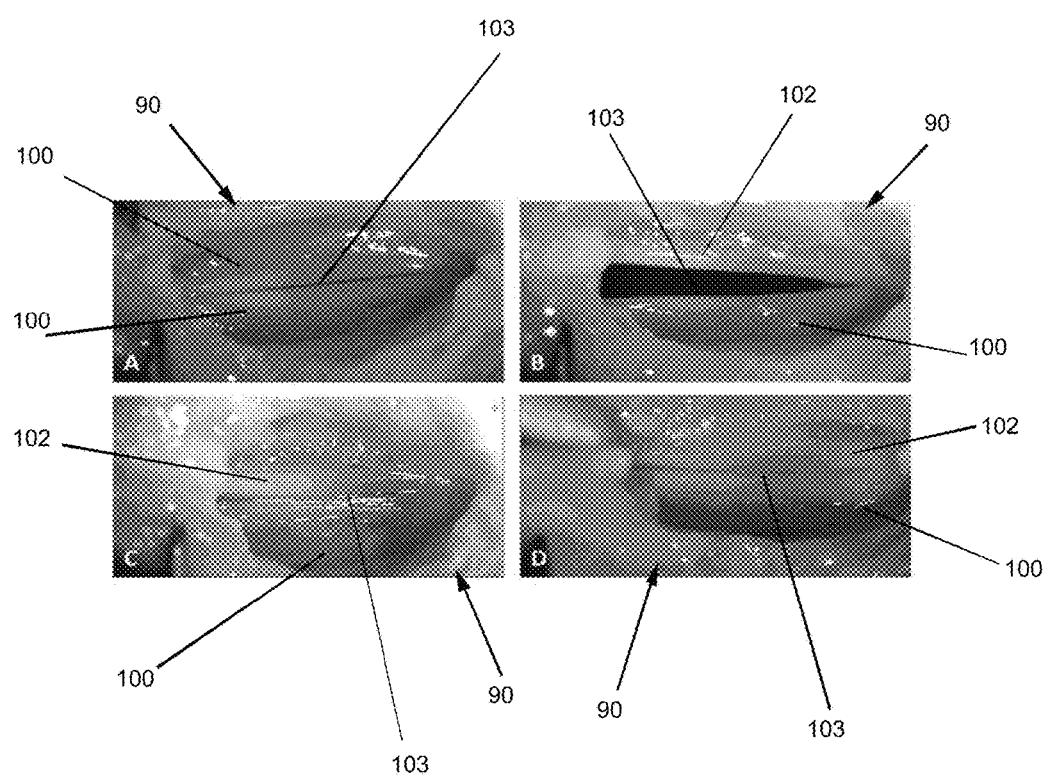
FIG. 1 are images showing a superior view of the larynx having a vocal fold midline and images and vocal fold position for a normal larynx (A), a larynx with vocal fold paralysis (B), a larynx after traditional arytenoid adduction (C), and a larynx after anterior arytenoid adduction (C).

As shown in FIG. 1, vocal folds 100 are two elastic bands of muscle tissue located in the larynx directly above the trachea. When you breathe, your vocal folds remain apart and when you swallow, they are tightly closed in a medial position 103 (as shown in view A, C and D of FIG. 1). When you use your voice, however, air from the lungs causes your vocal folds to vibrate between open and closed positions. VFP is a voice disorder that occurs when one or both of the vocal folds don't open or close properly. An example of VFP is shown in view B of FIG. 1 where the paralyzed fold 102 remain open, when the other vocal fold 100 is an a medial 103 position, leaving the air passages and lungs unprotected.

Figure 5:
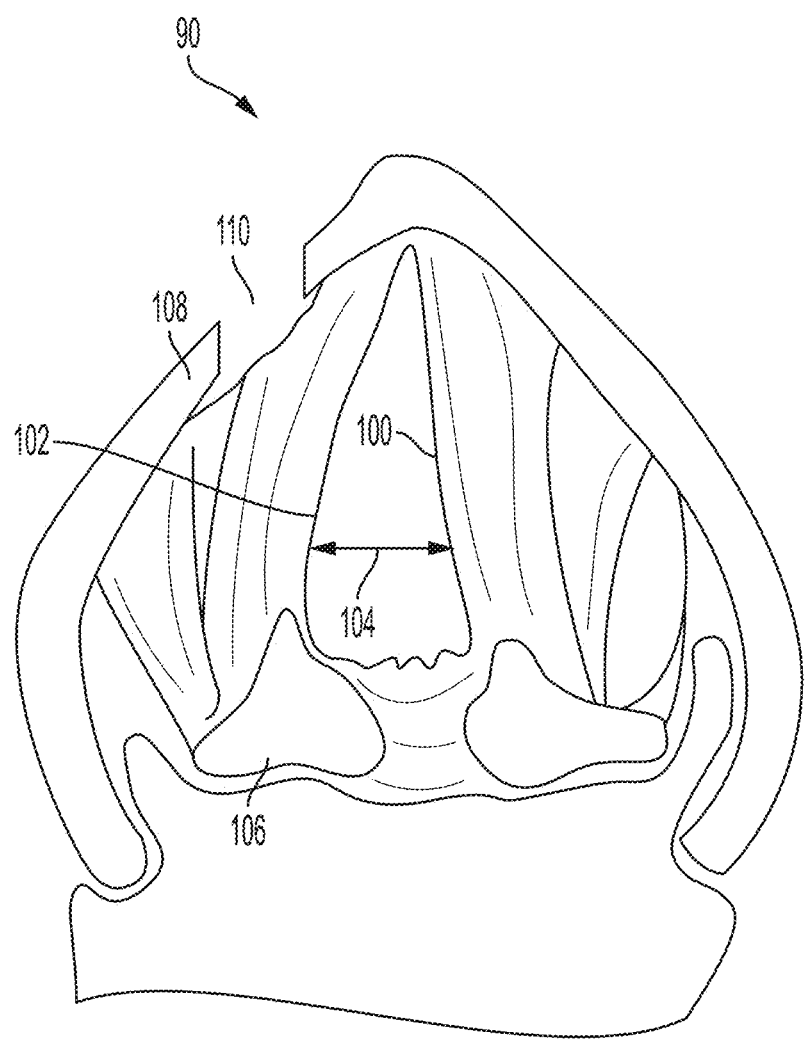
FIG. 5 is a schematic showing a superior view of a larynx (anterior is at top, posterior is at bottom) with left vocal fold paralysis (left side of page).

Another view of this is shown in FIG. 5. FIG. 5 is a schematic superior view of a larynx 90 (anterior is at the top of the image and posterior is at the bottom) with left vocal fold paralysis (right side of the image) with a normal vocal fold 100 and paralyzed vocal fold 102. A glottal gap 104 can form, when the vocal folds are normally in a "closed"

position. Normally, the vocal folds 100 are symmetric and approximate perfectly at the midline when in a "closed" position. As shown in FIG. 5, the paralyzed vocal fold 102 is smaller than the normal vocal fold 100 due to atrophy. The arytenoid cartilage 106 is ipslateral to the paralyzed vocal fold 102.

Arytenoid adduction is a process of manipulating the arytenoid cartilage associated with the paralyzed vocal fold, such that it medializes the paralyzed vocal fold. Conventional methods of AA approach the arytenoid posteriorly. Rather than approaching the muscular process of the arytenoid posteriorly, the devices disclosed herein may be used for an anterior approach to the arytenoid. As described in the Examples, objective and quantitative evidence from preliminary excised larynx experiments demonstrate that the methods and devices disclosed herein could eliminate the hardest part of the arytenoid adduction procedure, i.e., accessing the posterior larynx, and can transform arytenoid adduction from a long and highly invasive procedure done in the operating room to a much shorter and minimally invasive procedure that may be done in the clinic. Further disclosed in the Examples is objective evidence using quantitative aerodynamic and acoustic parameters confirming that this method improves laryngeal function to roughly the same degree as traditional AA.

As used herein, the term "arytenoid" refers to the arytenoid cartilage of a patient. The term "muscular process" refers the muscular process of the arytenoid cartilage and the soft tissues associated with this muscular process. Thus when referring to any connection to the "muscular process", refers to a connection to either the muscular process directly, or the soft tissues associated with the muscular process.

In one aspect of the present invention, a device is provided for arytenoid adduction. An example of the device 10 is shown in FIGS. 2-4 and 25-29. The device 10 comprises a suture wire complex 20 which comprises a wire hook complex 22 connected to a suture 24. The suture wire complex 20 comprises a wire 30 having a first end 32 and a second end 34 at opposite ends of a longitudinal axis 36. The wire 30 forms a spiral 38 along the longitudinal axis 36. The wire 30 has a hook 40 at the first end 32. The wire hook 40 can be in the form of a single hook, double hook, barb, or any suitable structure that would secure into the tissue of a patient. The suture 24 can be connected to the wire hook 40 by any suitable means. In certain embodiments, a suture 24 is threaded through the spiral 38 of the wire 30 from the second end 34 to the first end 32. The suture 24 forms a turn 44 at the first end 32 and then passes exterior to the spiral 38 to the second end 34, forming the suture wire complex 20. The suture 24 may be made of any suitable material known in the art. For example, the suture 24 may comprise Gore-Tex.

Figure 3:
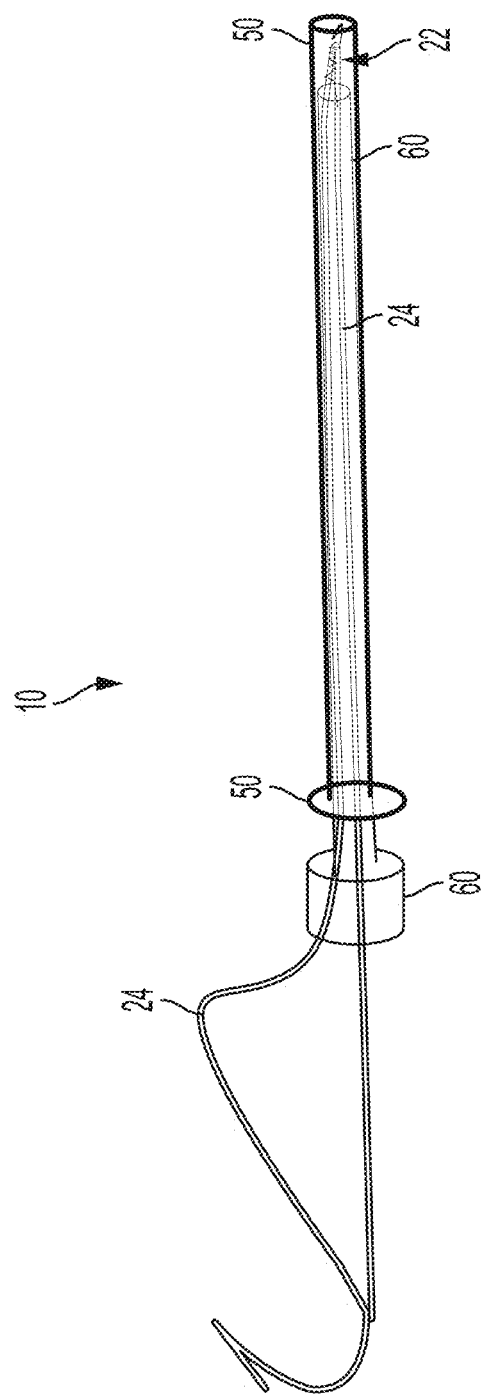
FIG. 3 is a schematic diagram of a device disclosed herein.
Figure 4:
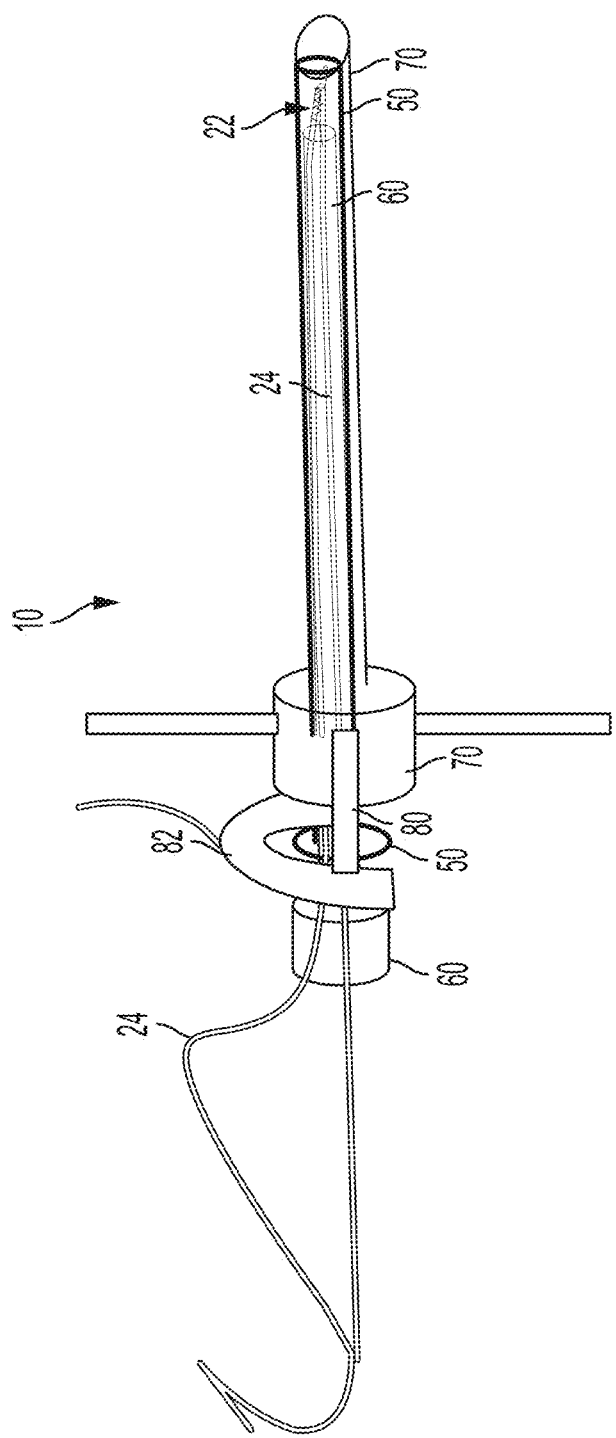
FIG. 4 is a schematic diagram of another embodiment of the device disclosed herein.
Figure 25:
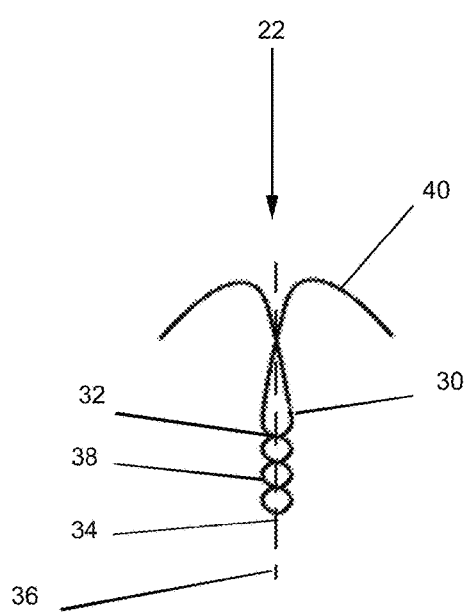
FIG. 25 shows one embodiment of the wire complex of the present invention with the hook in an open position.
Figure 26:
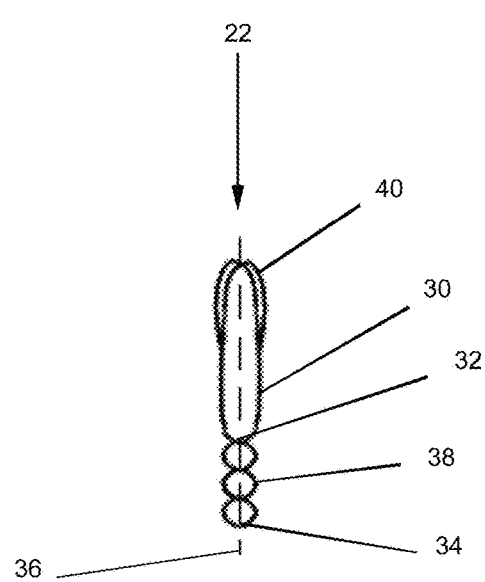
FIG. 26 shows one embodiment of the wire complex of the present invention with the hook in a closed folded position.
Figure 27:
FIG. 27 shows an embodiment of the suture wire complex with the hook in an open position.
Figure 28:
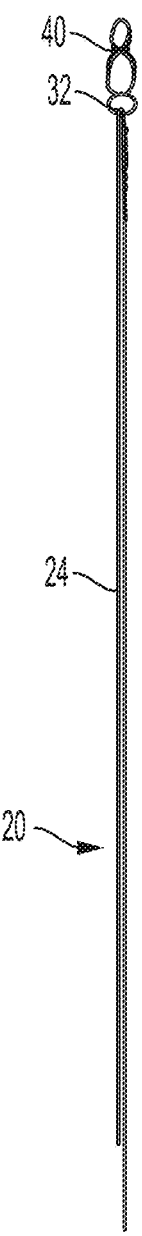
FIG. 28 shows an embodiment of the suture wire complex with the hook in a closed folded position.
Figure 29:
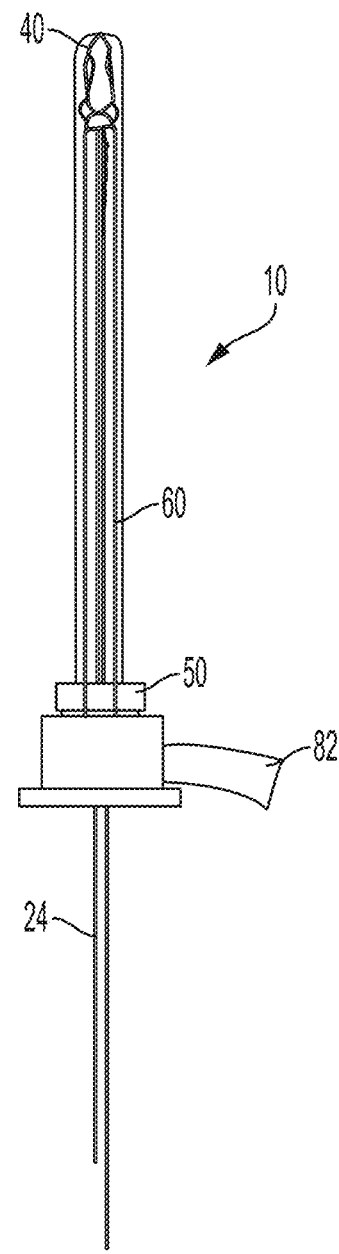
FIG. 29 shows an embodiment of the device with the hook in a closed folded position and inside the first guide needle.

The device 10 may further comprise a first needle 50 enclosing the suture wire complex 20, as best shown in FIG. 3. In the example described in FIGS. 6-23 the first needle 50 is acting as a guide needle, though a separate larger guide needle can be used, that can enclose the first needle 50. As used herein the term "needle" refers to any elongated structure with a hollow center, which can include catheters, needles, tubes, or other such structures. The first needle 50, may be any suitable gauge. In one embodiment the gauge of the first needle 50 is between about 12 to about 16, more suitably the gauge is about 14. The device 10 may further comprise a second needle 60 enclosed by the first needle 50. The second needle 60 may be of any gauge smaller than the first needle 50, suitably between about 18 to about 22, more suitably a gauge of about 20. The first needle 50 is suitably of diameter to enclose the suture wire complex 20 and also enclose the second needle 60. The second needle 60, in certain embodiments, may partially enclose the suture-wire complex 22 and acts as a hook extrusion device, the second needle 60 being used to push the hook to the exterior of any enclosing structures such as the first needle 50. In certain embodiments, when the wire complex 22 is enclosed by a structure, the hook is designed to close to a folded position as shown in FIGS. 26, 28 and 29. When the wire complex is moved outside of any enclosing structure, the hook expands to an open configuration as shown in FIGS. 25 and 27 that can be hooked to a structure. The second needle 60 may include a protective cover 82 to go between the first needle 50 and the second needle 60 to ensure the suture wire complex 20 is not passed too far in the subject.

Figure 6:
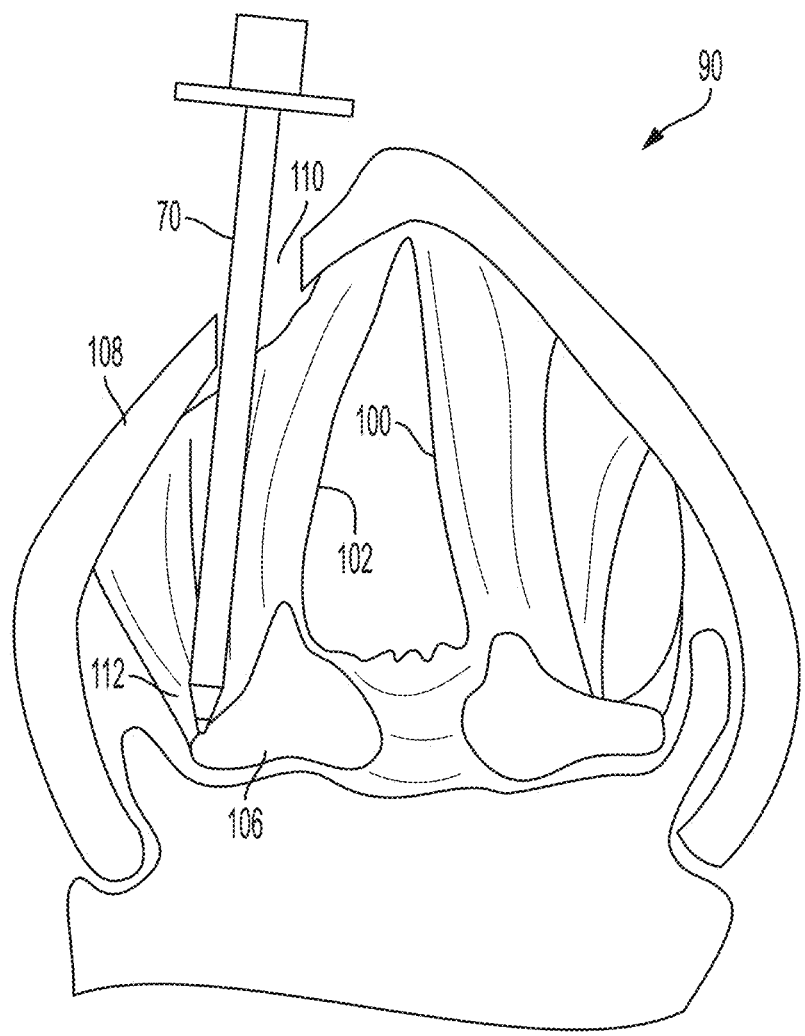
FIG. 6 is a perspective view of the initial localizing trocar being passed through the paraglottic tissue of the larynx to the muscular process of the arytenoid.

The device 10 may further include additional components including, for example, a trocar 70 enclosing the first needle 50, as shown in FIG. 6. A localizing trocar 70 with a light 80 fiber could be added to allow for visualization of the muscular process 112 during the procedure. (See FIG. 7). A protective guard could be added to cover the larger (e.g., 14-gauge) needle to ensure it does not advance until the muscular process 112 has been reached.

Figure 16:
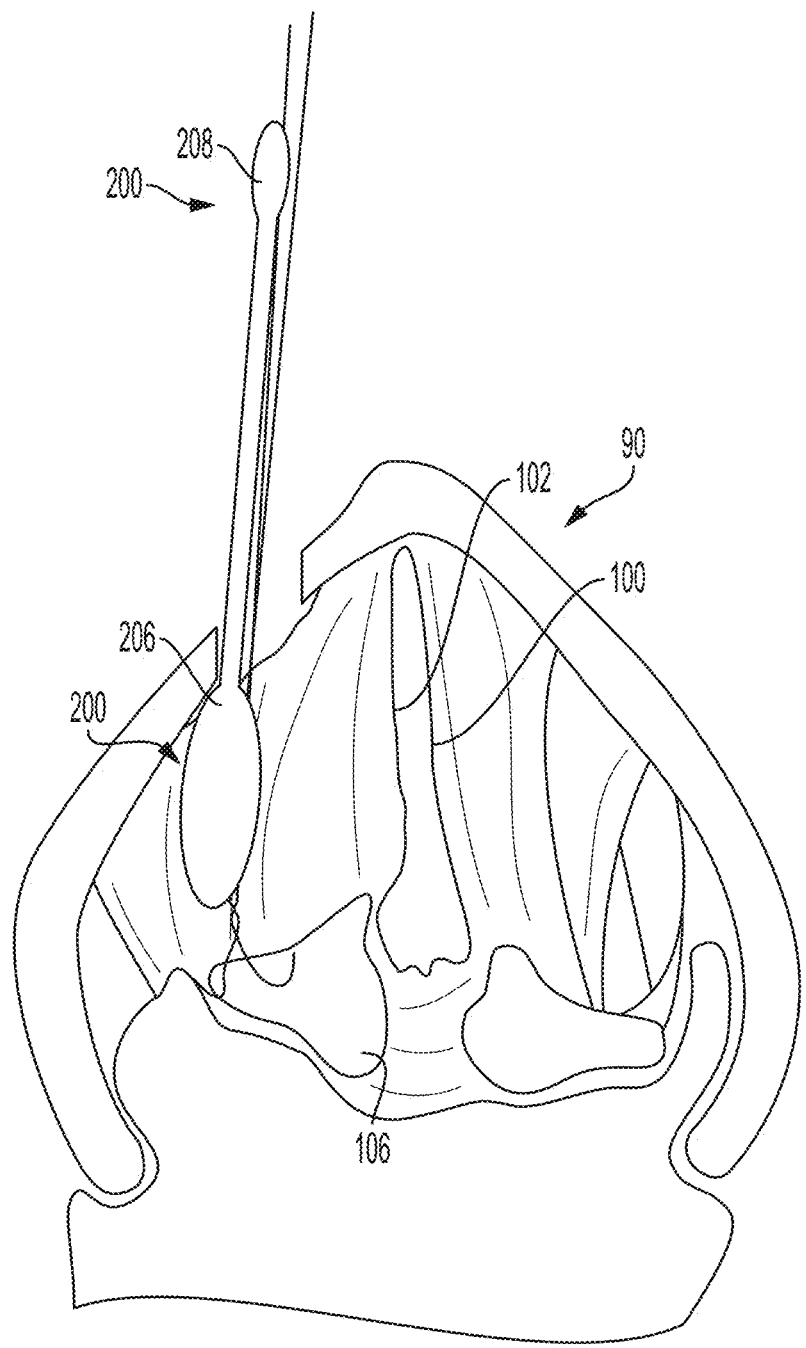
FIG. 16 is a schematic superior view of the larynx, where one embodiment of the suture wire complex of the present invention has been used to rotate the arytenoid of the paralyzed vocal fold. A thyroplasty implant with hollow center has also been passed down one of the suture strands to provide bulk to the paralyzed vocal fold.
Figure 17:
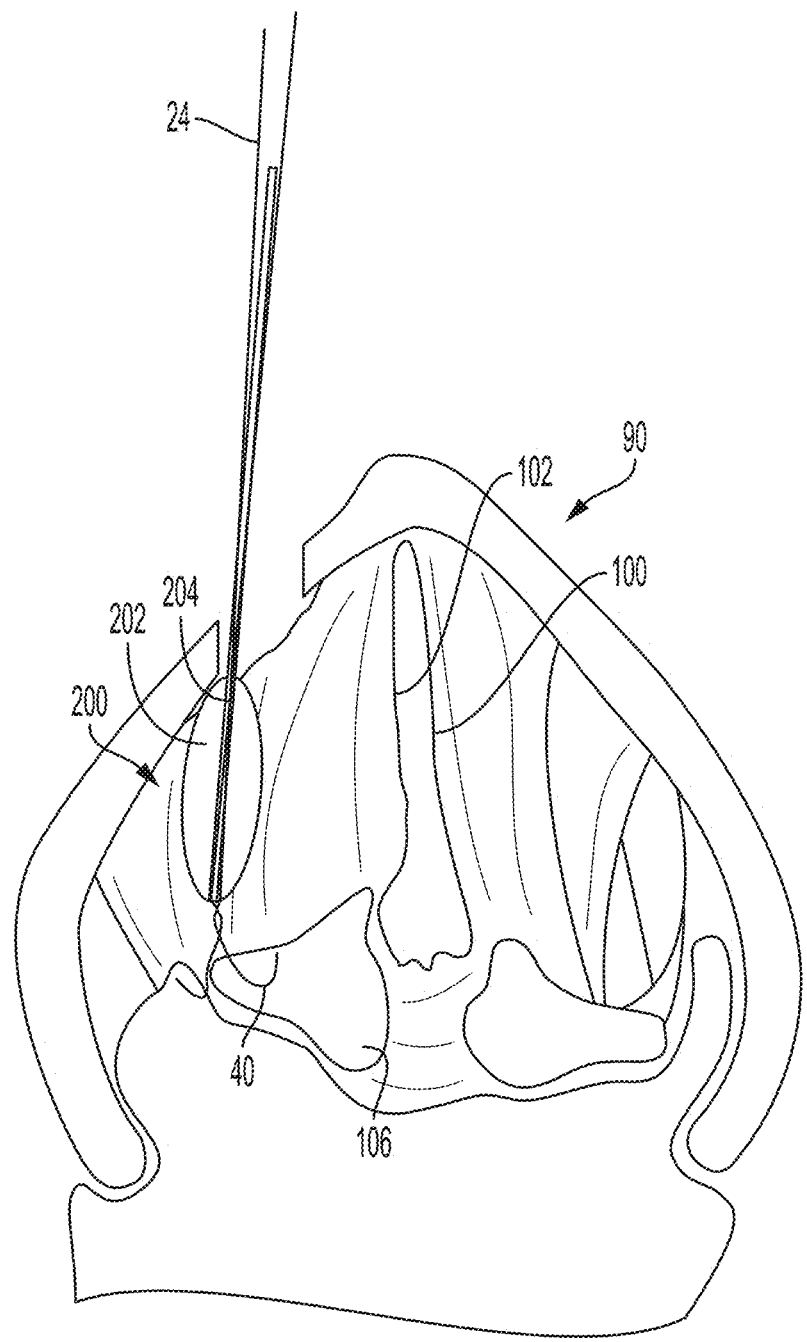
FIG. 17 is a schematic superior view of the larynx, where one embodiment of the suture wire complex of the present invention has been used to rotate the arytenoid of the paralyzed vocal fold and a thyroplasty implant has been passed along one of the suture strands to provide bulk to the vocal fold.
Figure 21C:
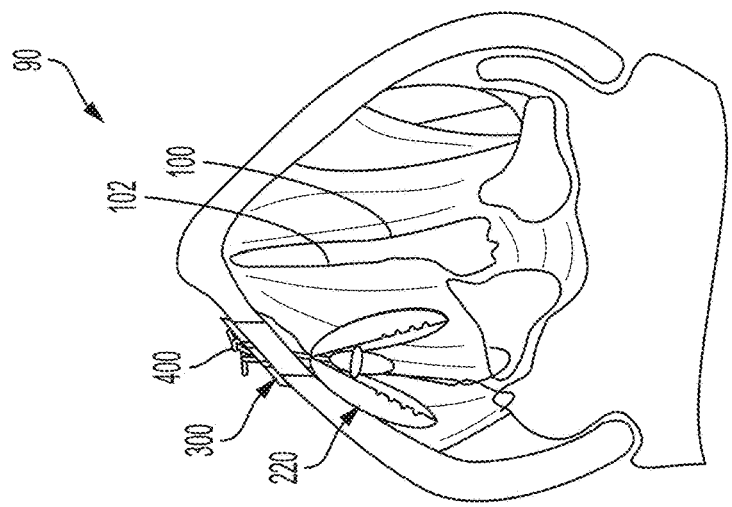
FIG. 21c is a schematic superior view of the larynx, where an embodiment of the suture wire complex of the present invention has been used to rotate the arytenoid of the paralyzed vocal fold and an expanding thyroplasty implant in an expanded position has been passed along one of the suture strands to provide bulk to the vocal fold, and the ends of the sutures are tied together outside a thyroid cartilage reconstruction device.
Figure 21B:
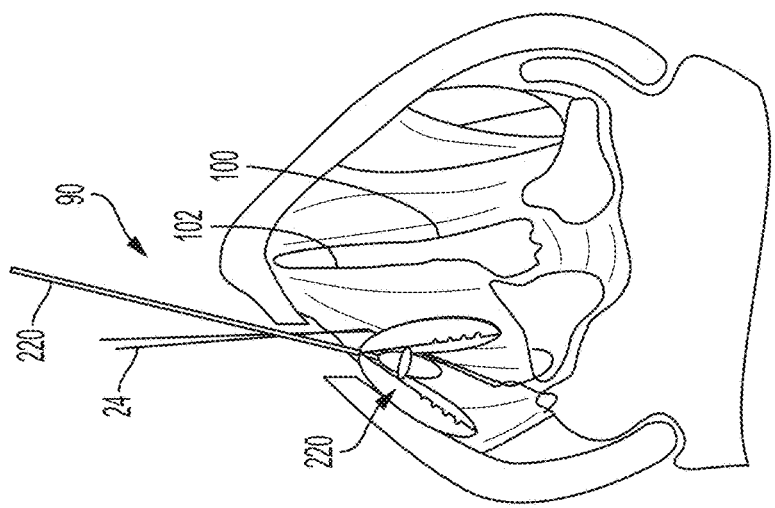
FIG. 21b is a schematic superior view of the larynx, where an embodiment of the suture wire complex of the present invention has been used to rotate the arytenoid of the paralyzed vocal fold and an expanding thyroplasty implant in an expanded position has been passed along one of the suture strands to provide bulk to the vocal fold.
Figure 21A:
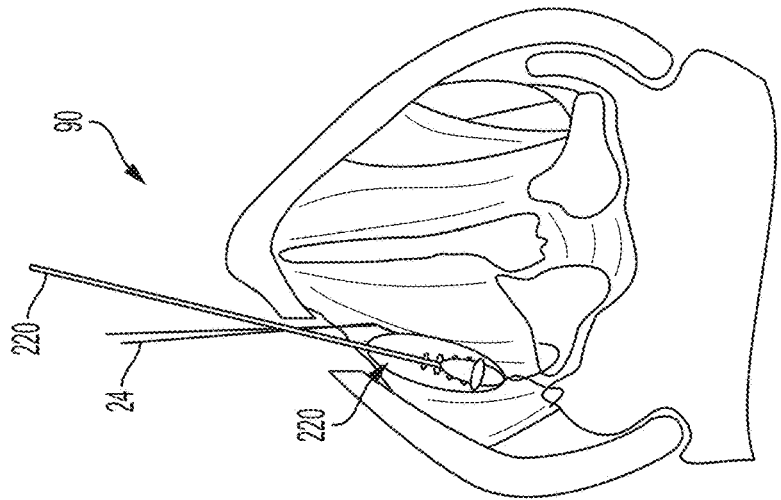
FIG. 21a is a schematic superior view of the larynx, where an embodiment of the suture wire complex of the present invention has been used to rotate the arytenoid of the paralyzed vocal fold and an expanding thyroplasty implant in a closed position has been passed along one of the suture strands.
Figure 22C:
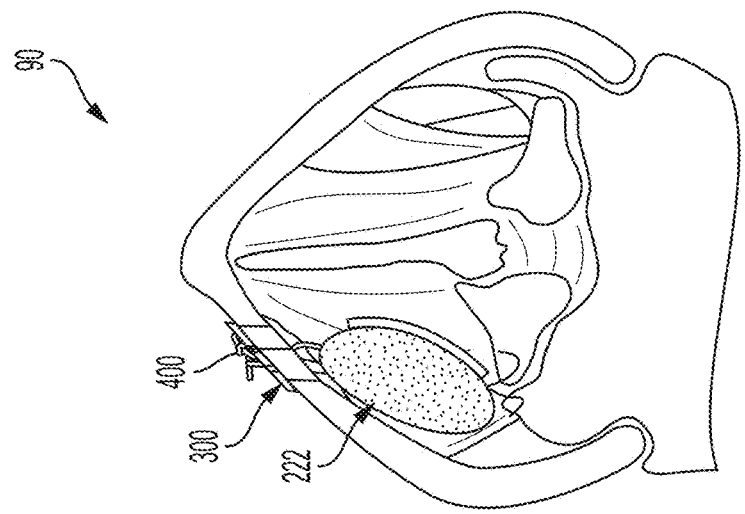
FIG. 22c is a schematic superior view of the larynx, where an embodiment of the suture wire complex of the present invention has been used to rotate the arytenoid of the paralyzed vocal fold and an inflatable thyroplasty implant in an inflated position has been passed along one of the suture strands to provide bulk to the vocal fold, and the ends of the sutures are tied together outside a thyroid cartilage reconstruction device.
Figure 22B:
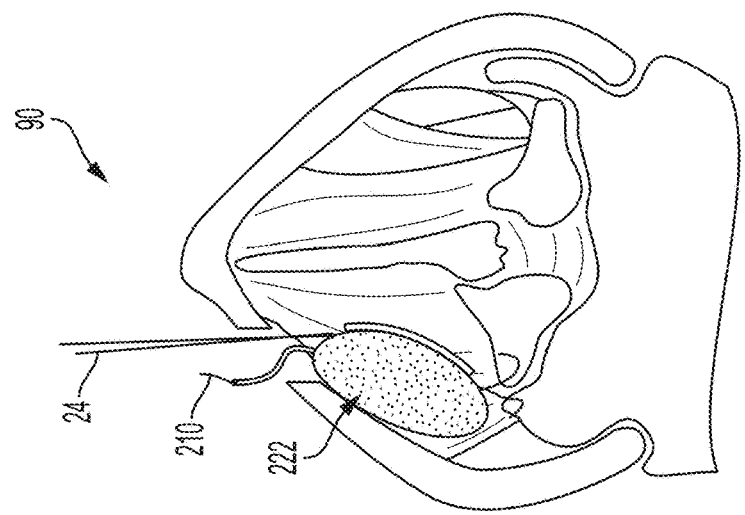
FIG. 22b is a schematic superior view of the larynx, where an embodiment of the suture wire complex of the present invention has been used to rotate the arytenoid of the paralyzed vocal fold and an inflatable thyroplasty implant in an inflated position has been passed along one of the suture strands to provide bulk to the vocal fold.
Figure 22A:
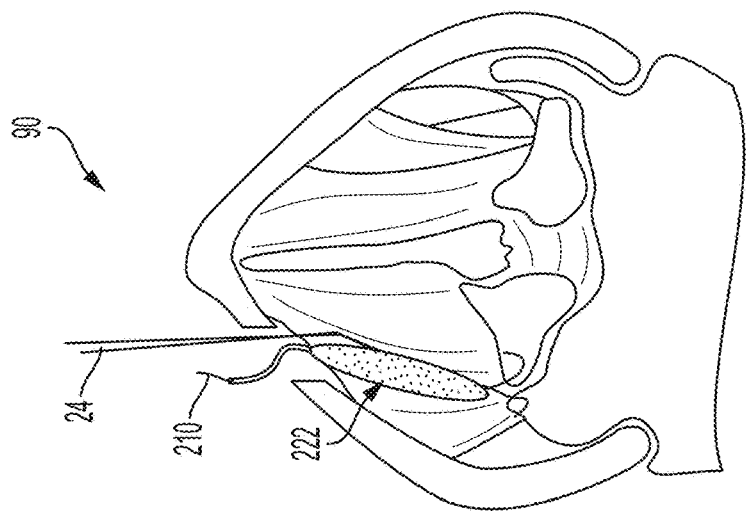
FIG. 22a is a schematic superior view of the larynx, where an embodiment of the suture wire complex of the present invention has been used to rotate the arytenoid of the paralyzed vocal fold and an inflatable thyroplasty implant in a deflated position has been passed along one of the suture strands.

The device 10 may also include a thyroplasty implant (as shown in FIG. 17). The thyroplasty implant can positioned by the suture wire complex 20 (as described below) to provide bulk to a paralyzed vocal fold 102 to aid in medializing the fold. The thyroplasty implant 200 can be any suitable implant for this purpose, including a multipart implant 206 and 208 (as shown in FIG. 16), an explanting implant 220 (as shown in FIG. 21), or an inflatable implant 222 (as shown in FIG. 22). In one embodiment, the thyroplasty implant 200 is a solid body 202 having a central aperture 204 so as to allow it to be slid down the suture 24 and positioned appropriately. The body of the thyoplasty implant 200 can be any suitable material. Examples of suitable materials include solid Medpore, silastic material, porous polyethylene, or gold material.

Figure 18:
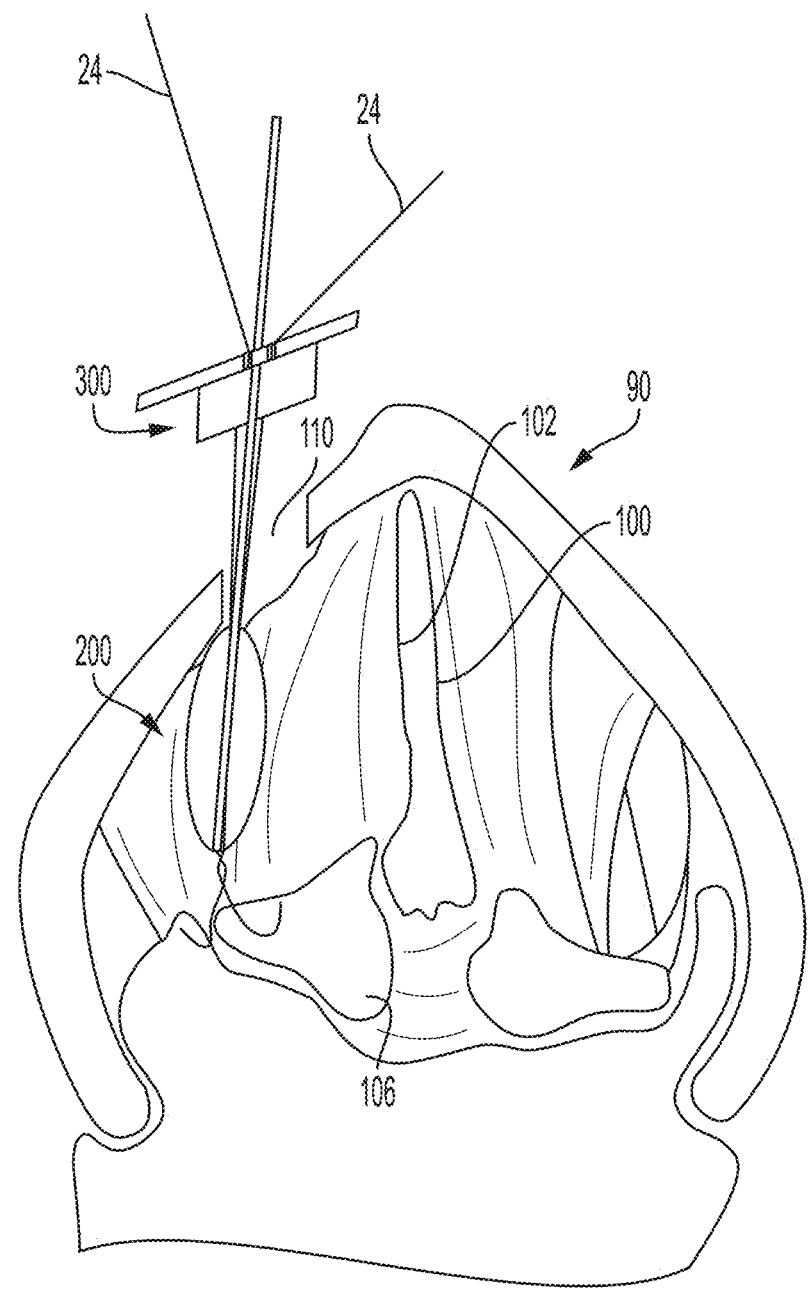
FIG. 18 is a schematic superior view of the larynx, where one embodiment of the suture wire complex of the present invention has been used to rotate the arytenoid of the paralyzed vocal fold and a thyroplasty implant has been passed along one of the suture strands to provide bulk to the vocal fold and a reconstruction device is being placed to cover the incision damage to the thyroid cartilage.
Figure 20:
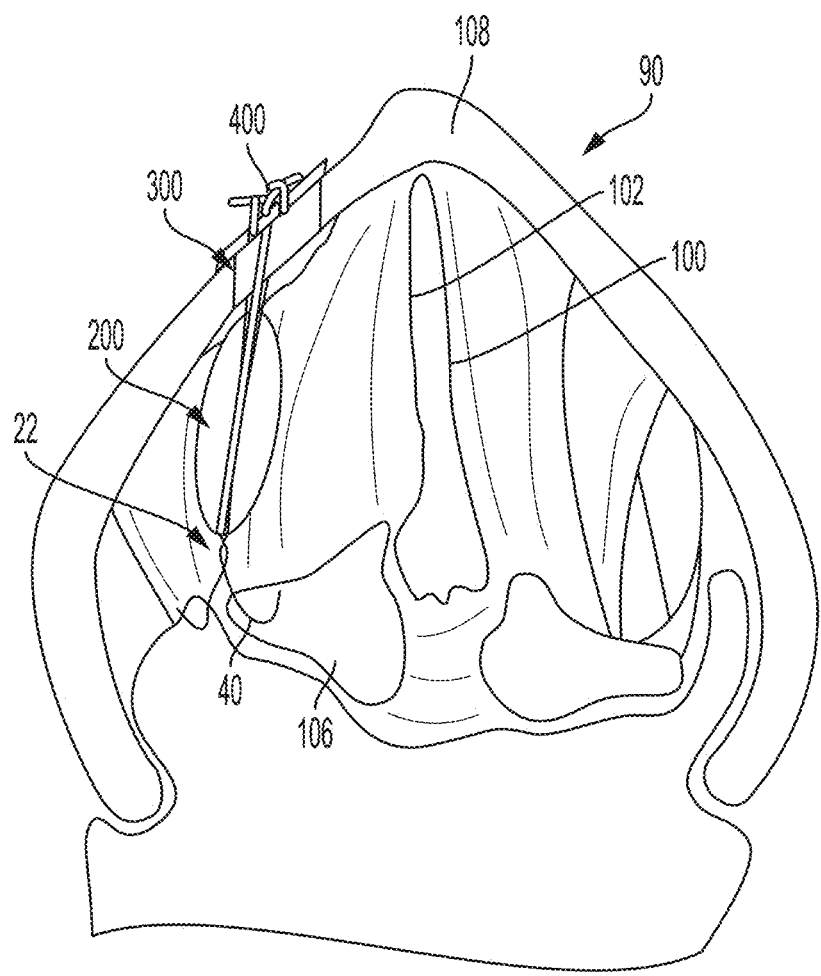
FIG. 20 is a schematic superior view of the larynx, where one embodiment of the suture wire complex of the present invention has been used to rotate the arytenoid of the paralyzed vocal fold and a thyroplasty implant has been passed along one of the suture strands to provide bulk to the vocal fold and a reconstruction device has repair the incision damage to the thyroid cartilage with the ends of the suture tied together outside the thyroid cartilage reconstruction device.

The device 10 may also include a reconstruction device 300 (as shown in FIGS. 18 and 20) that can be used to repair the aperture 110 made to the thyroid cartilage 108 during the AA procedure using the device 10. The reconstruction device 300 can be made of any suitable sturdy material. An example of a suitable material includes silastic materials. The reconstruction device 300 can also be used to secure the sutures 24 to secure the suture in place.

The device 10 can also include a drug delivery device (see FIG. 23) that can be advanced down the suture 24 of the suture wire complex 20 to allow for the delivery of drug compositions to an area targeted by the physician by the placement of the drug delivery device. Any suitable drug delivery mechanism can be used that can be positioned by way of the sutures 24. In one embodiment drug delivery beads 205 can be used.

In another embodiment, the device can include a void measuring device 275 see FIG. 24). The void measuring device can be used to measure the volume of a glottal gap 104. The void measuring device 275 in one embodiment includes an inflatable balloon 280 and a syringe 278. The inflatable balloon 280 is designed such that it can be advanced down the suture 24 of the suture wire complex 20 to allow for positioning of the inflatable balloon 280.

Methods of using the devices of the present invention will now be described.

In one aspect, a method of adducting an arytenoid 106 in a subject in need thereof is provided by utilizing the subject the device 10 as described above.

As shown in FIG. 5, a circular window 110 (about 5 mm to about 8 mm in diameter) is first drilled into the thyroid cartilage 108, allowing the surgeon to access the arytenoid 106 by the device 10.

Figure 7:
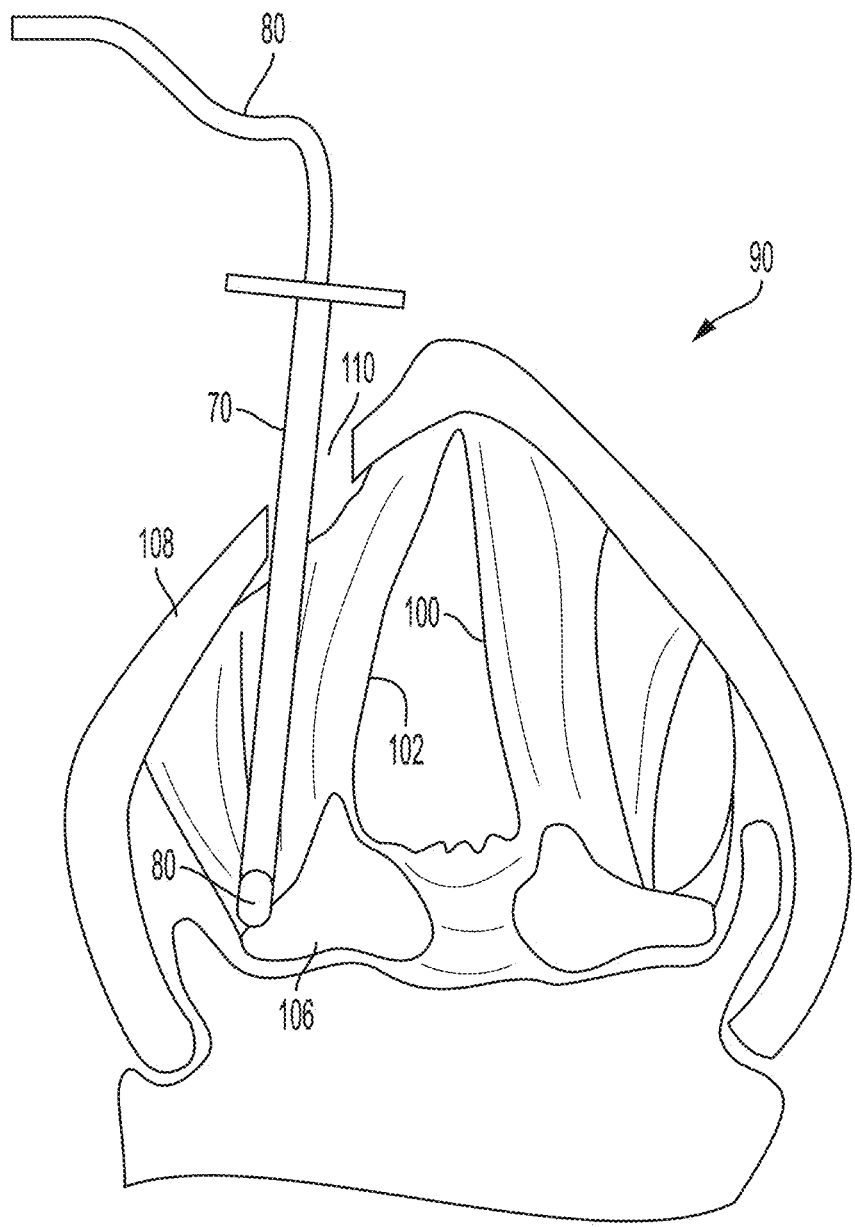
FIG. 7 is a perspective view of the light cable being passed through the localizing trocar.
Figure 8:
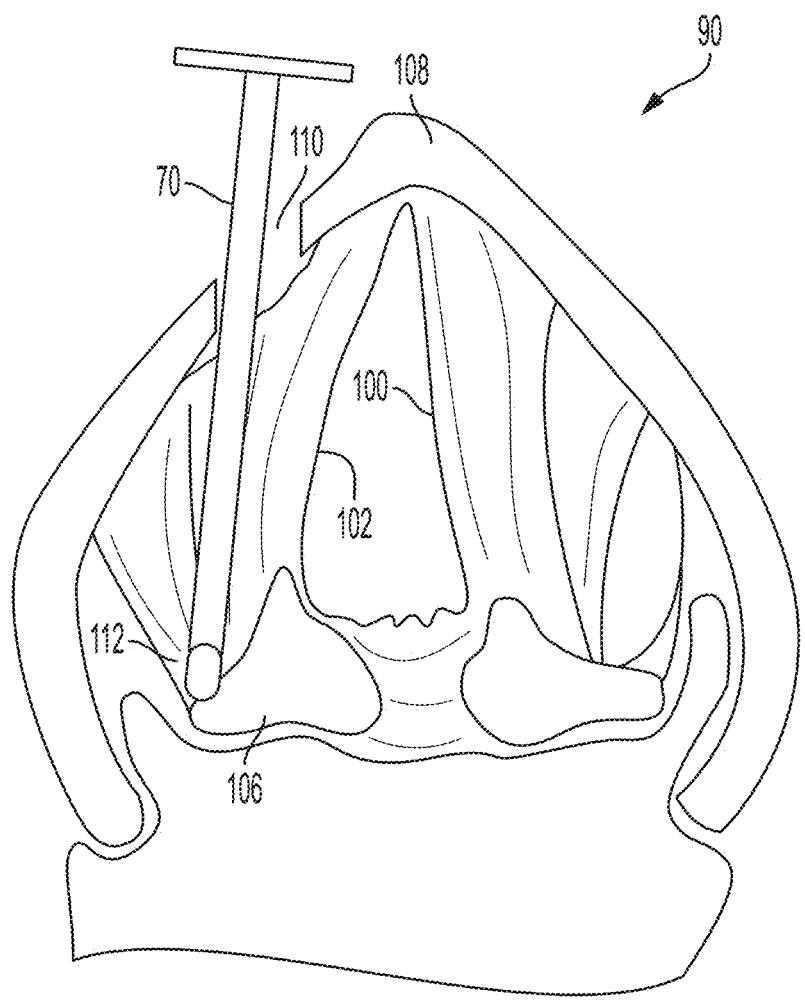
FIG. 8 is a perspective view of the larynx with the localizing trocar in the correct position as determined using the light cable and arytenoid motion.

As shown in FIG. 6, a device 10 comprising the suture wire complex 20 being enclosed by a trocar 70 is passed through the paraglottic tissue of the larynx 90 to the muscular process 112 of the arytenoid 106. As shown in FIG. 7, a light cable 80 can be advanced down the trocar 70 to allow the surgeon to visualize portions of the arytenoid 106 and muscular process 112. This ensures that the suture wire complex 20 will be positioned in the correct location. Simultaneous transnasal fiberoptic endoscopy and intraoperative voicing may be performed to evaluate vocal fold 100 position and laryngeal function. FIG. 8 shows that the localizing trocar 70 is positioned correctly; the suture wire complex 20 can be passed through it to manipulate the arytenoid cartilage 106.

Figure 9:
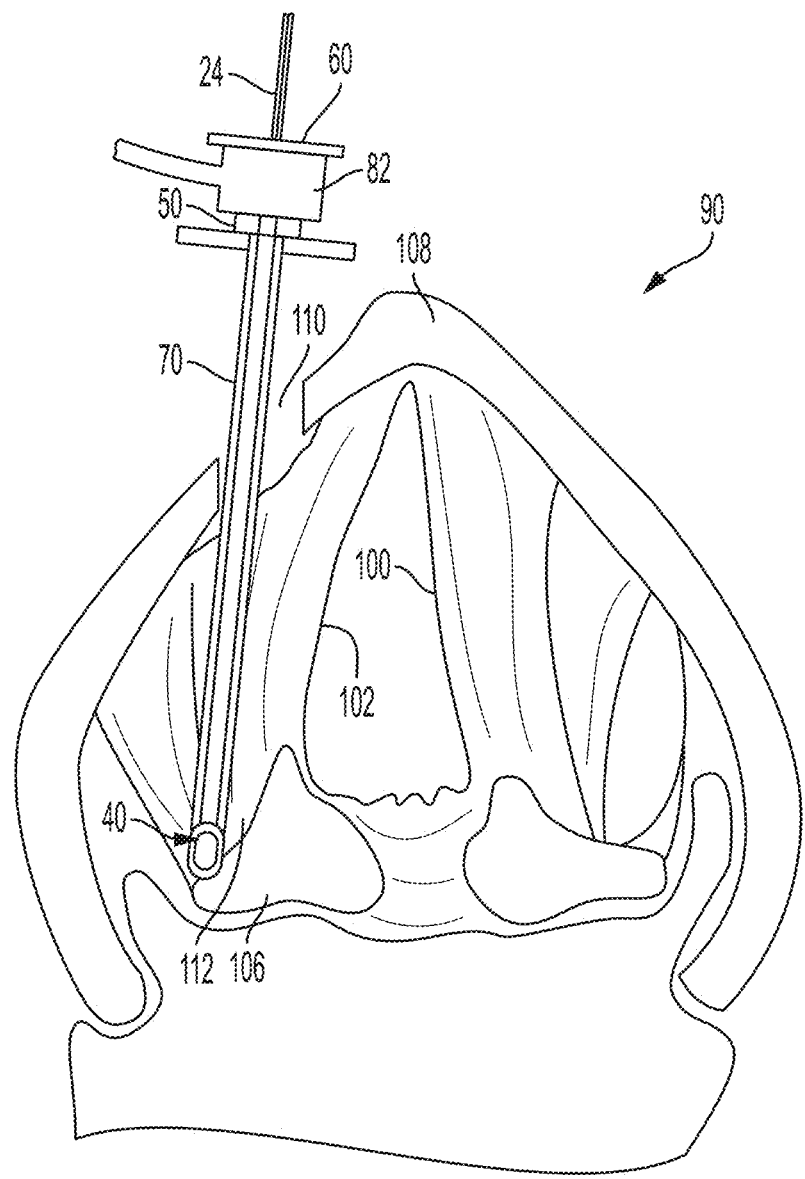
FIG. 9 is a schematic superior view of the larynx, where one embodiment of the suture wire complex of the present invention is being passed through the guide needle to the muscular process of the arytenoid.
Figure 10:
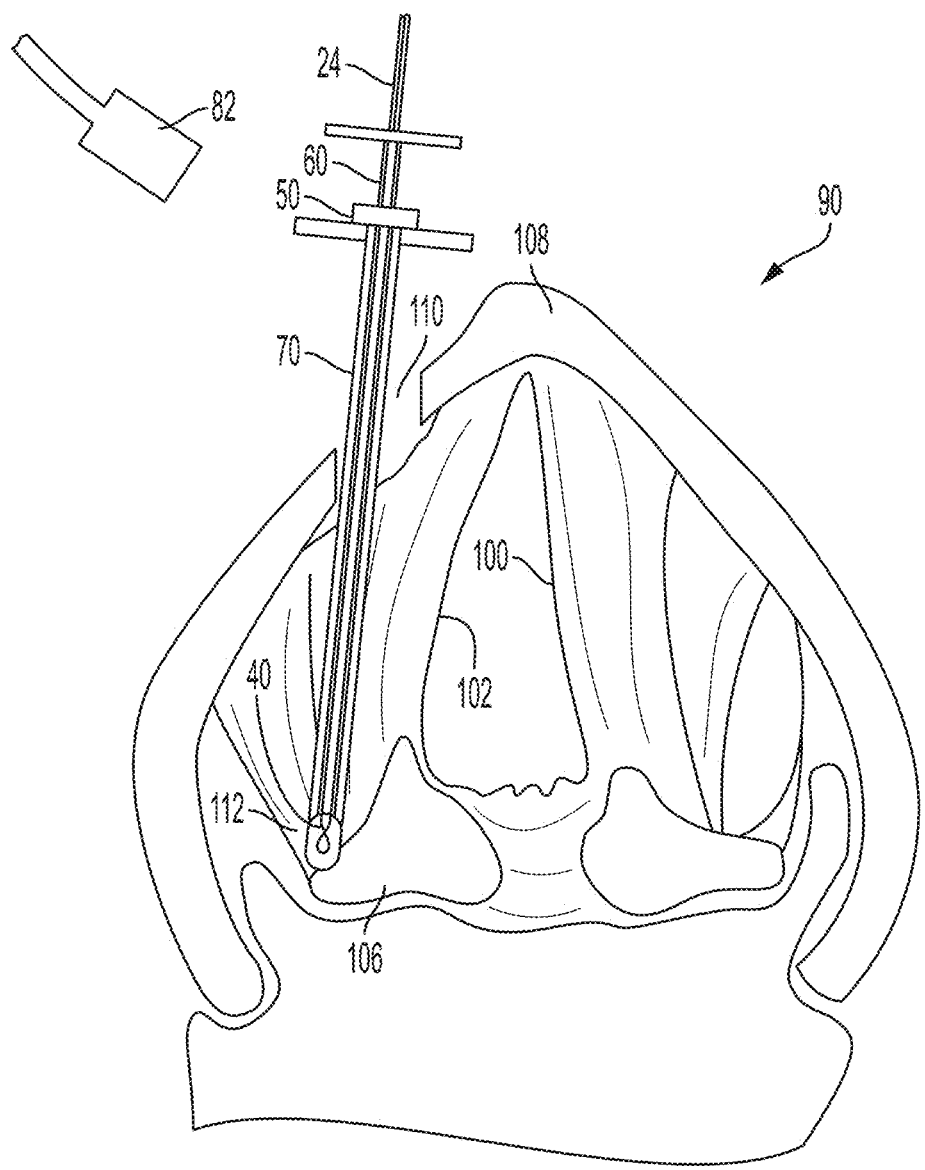
FIG. 10 is a schematic superior view of the larynx, where one embodiment of the suture wire complex of the present invention is being passed through the guide needle to the muscular process of the arytenoid.
Figure 11:
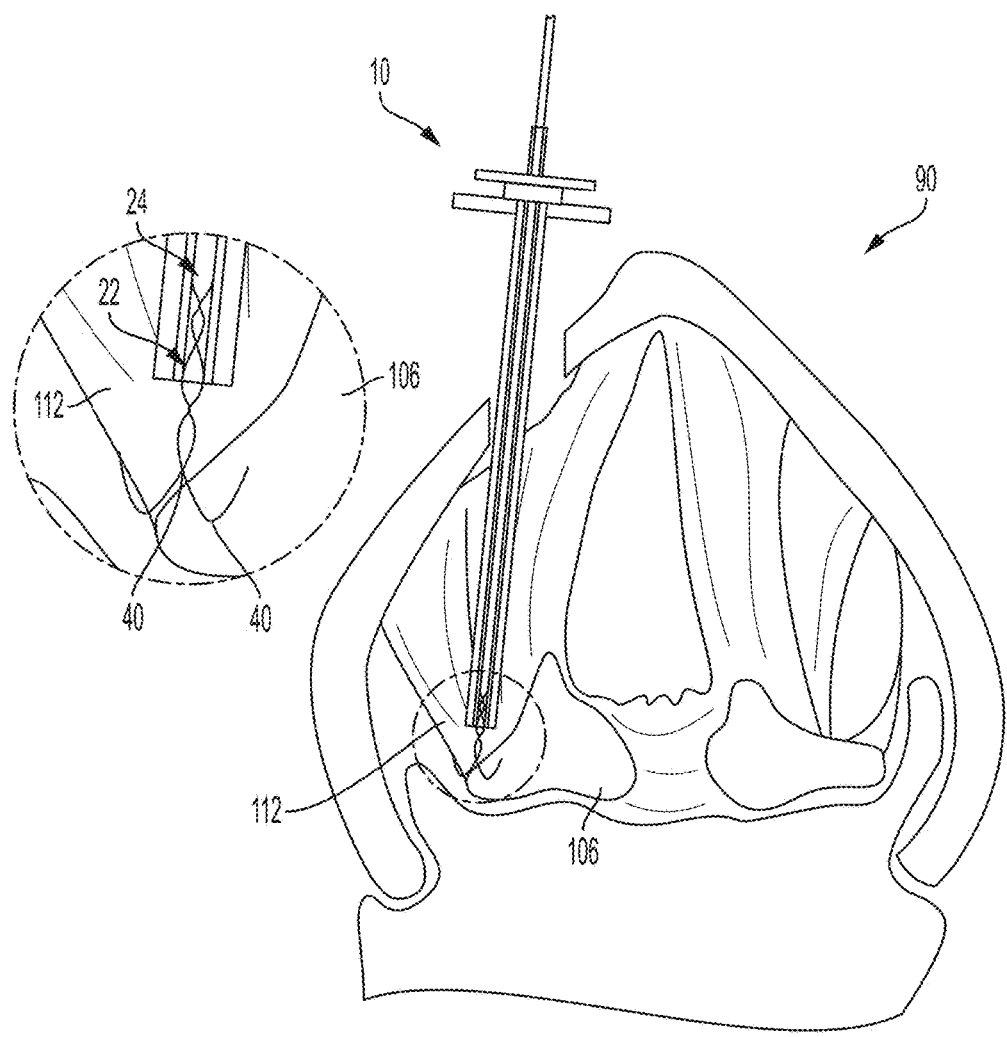
FIG. 11 is a schematic superior view of the larynx, where one embodiment of the suture wire complex of the present invention has been passed through the guide needle to the muscular process of the arytenoid. The circle inset is a close-up view, showing the hooked wires deployed and securely attached to the soft tissues surrounding the muscular process of the arytenoid.
Figure 12:
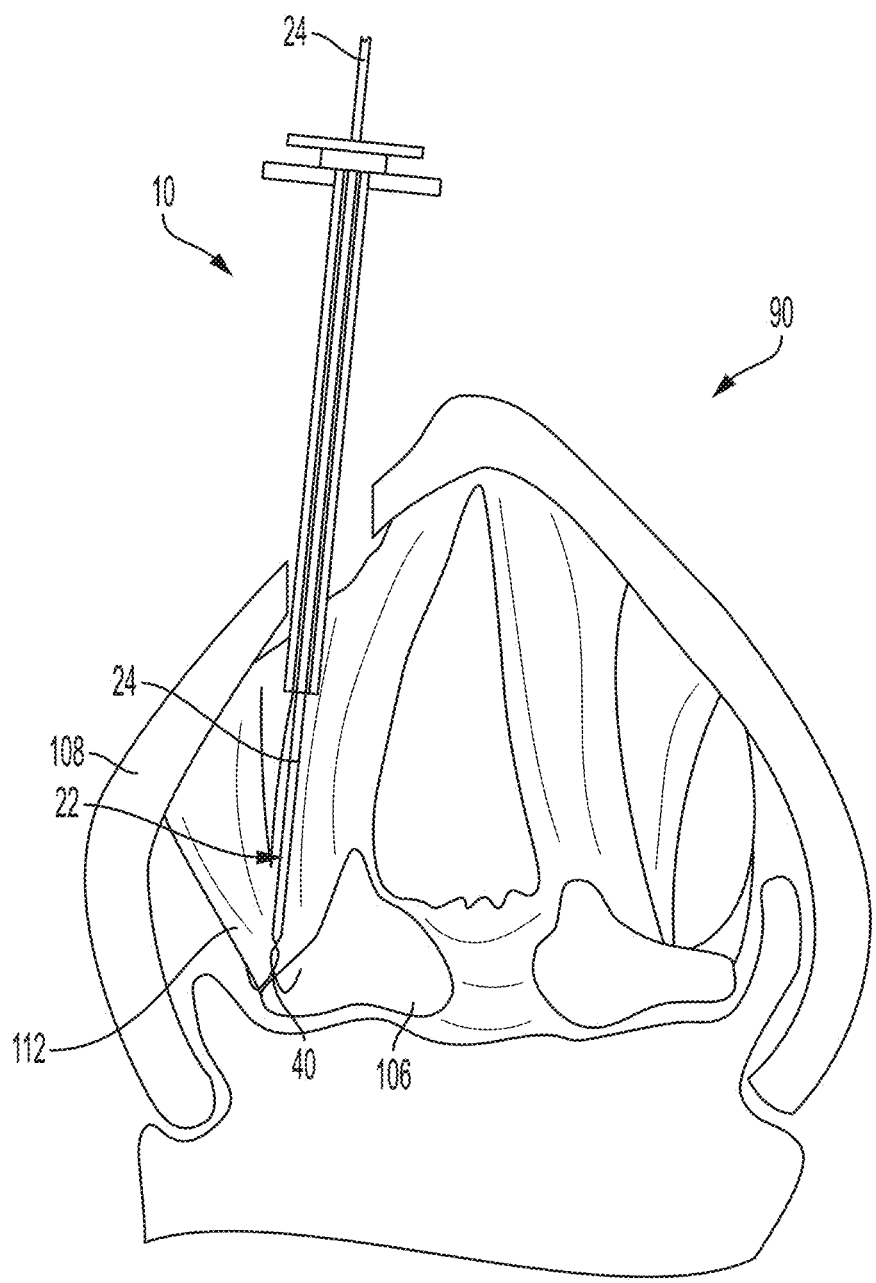
FIG. 12 is a schematic superior view of the larynx, where one embodiment of the suture wire complex of the present invention has been passed through the guide needle to the muscular process of the arytenoid. The guide needle is now being removed through the small hole created in the thyroid cartilage.
Figure 13:
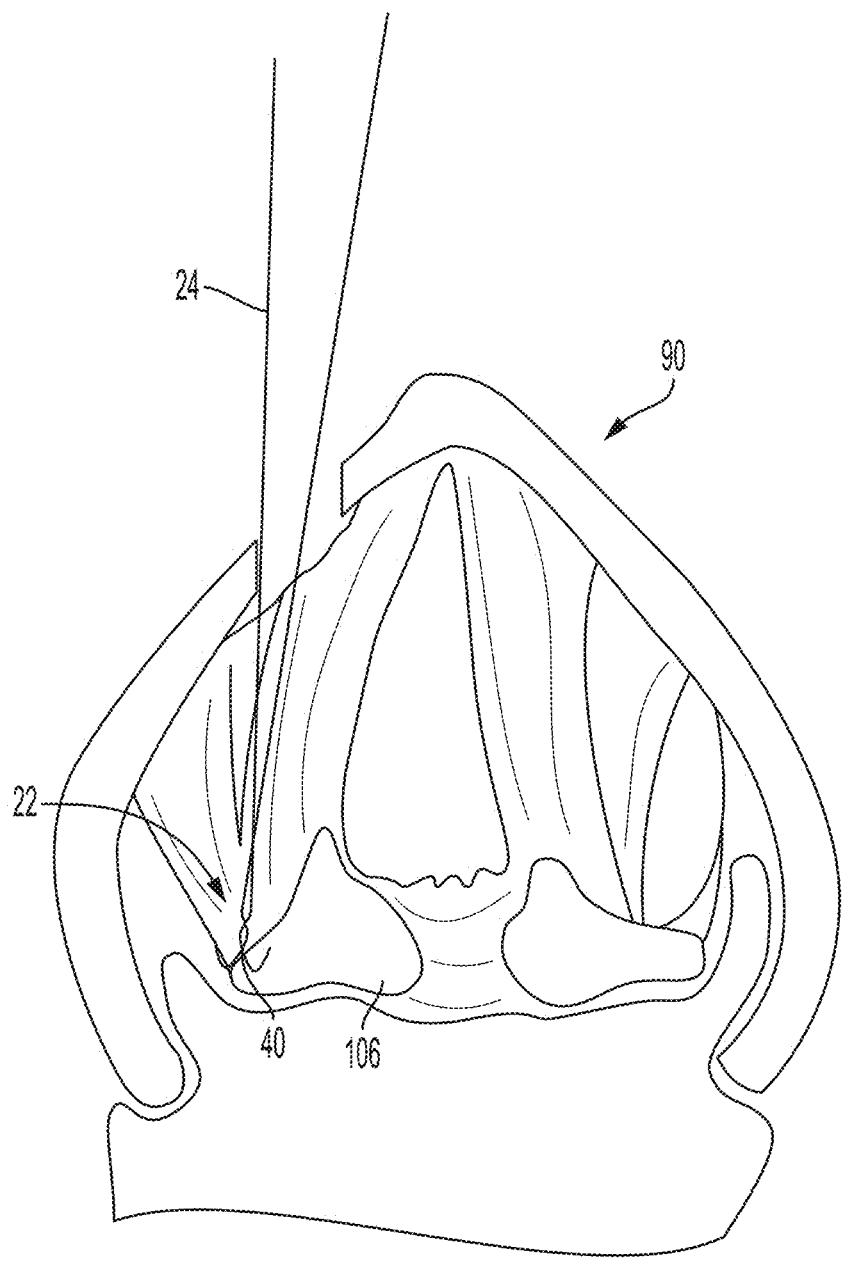
FIG. 13 is a schematic superior view of the larynx, where one embodiment of the suture wire complex of the present invention has been passed through the guide needle to the muscular process of the arytenoid. The guide needle has now been completely removed and now only the suture wire complex can be seen.

FIG. 9 shows that the suture wire complex 20 of the present invention is being passed through the first needle to the muscular process 112 of the arytenoid 106. In this embodiment, the suture wire complex 20 comprises the wire hook complex 22 having a hook 40, and a suture 24. The suture wire complex in located inside a second needle 60, which in turn is inside a first needle 50. A protective cover 82 is positioned between the tops of the first 50 and second 60 needles to ensure the suture wire complex 20 is not passed too far in the subject and result in a violated mucosa and passage of the complex beyond the larynx 90. The second needle is now used to finely position the hook 40 for placement. As shown in FIG. 10, the protective cover 82 is removed, and the hook 40 and suture 24 complex is passed though the needles 50 and 60 and is hooked in the appropriate position. FIG. 11 shows the hook 40 securely attached to the soft tissues surrounding the muscular process 112 of the arytenoid 106. As shown in FIGS. 12 and 13, the needles, 50 and 60, and the trocar 70 are now removed, leaving the suture wire complex in the patient.

Figure 14:
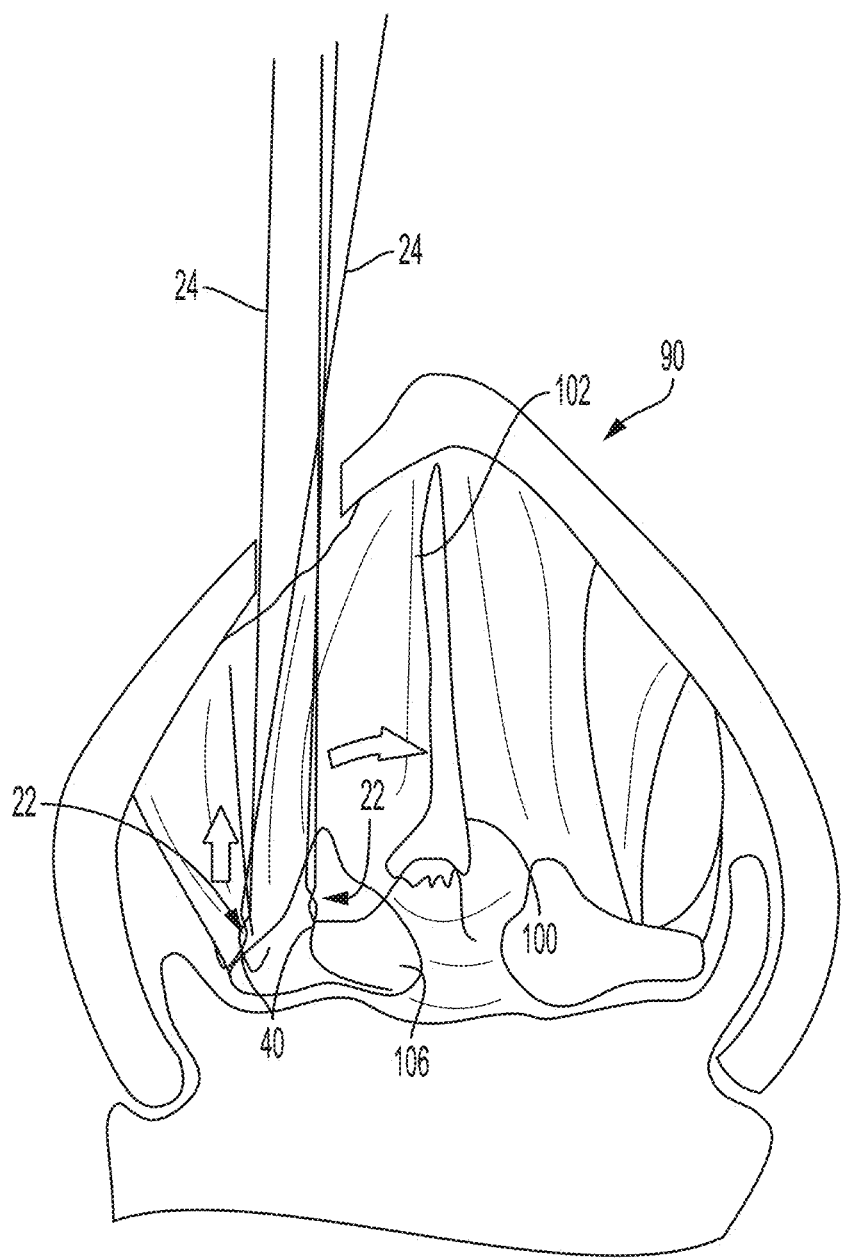
FIG. 14 is a schematic superior view of the larynx, where one embodiment of the suture wire complex of the present invention is being used to rotate the arytenoid of the paralyzed vocal fold. The arrows show the direction of arytenoid rotation inward, which medializes the paralyzed vocal fold.
Figure 15:
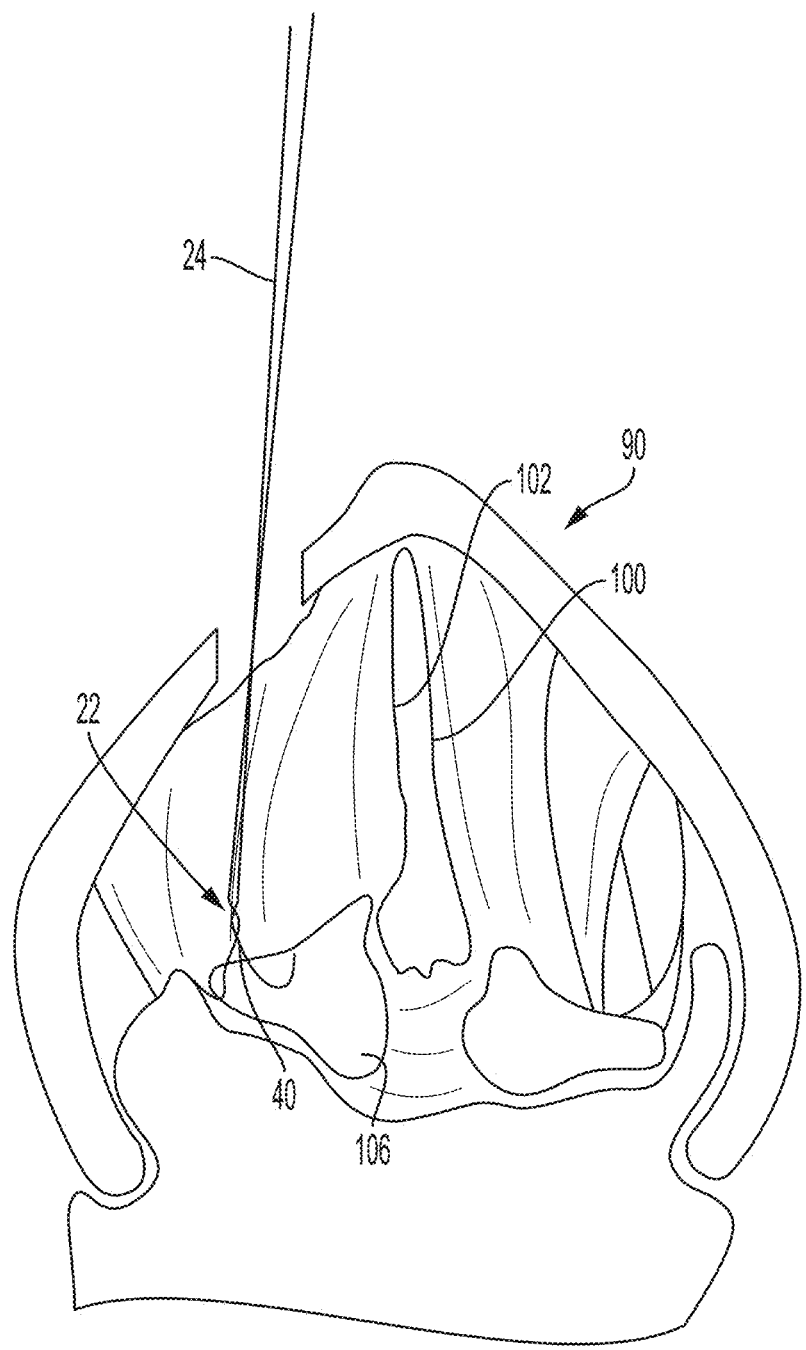
FIG. 15 is a schematic superior view of the larynx, where one embodiment of the suture wire complex of the present invention has been used to rotate the arytenoid to the paralyzed vocal fold.

As shown in FIG. 14, tension is now applied to the suture 24 to rotate the arytenoid 106 ipsilateral to the paralyzed vocal fold 102, thus adducting the arytenoid 106. The arrows show the direction of arytenoid 106 rotation inward, which medializes the paralyzed vocal fold 102. FIG. 15 shows the fully rotated arytenoid 106. The arytenoid 106 is now in a position conducive to voice production. Note that while the arytenoid 106 has been rotated, medializing the vocal fold 100, there is still a space between the vocal fold 100 and the paralyzed vocal fold 102 due to the atrophy that can occur with longstanding paralysis.

In one embodiment of the device 10, the device can include the use and placement of a thyroplasty implant 200. One example of how this procedure can be accomplished is shown in FIGS. 16-20. A thyroplasty implant 200 comprising two parts, a large section 206 and a small section 208, both having a hollow center 204 is provided. The large section 206 has been passed down one of the suture strands 24 to provide bulk to the paralyzed vocal fold 102. In this embodiment, the smaller section implant 208 is passed along the suture 24 which will reside inside the larger section 206 to provide additional firmness and bulk without requiring a larger defect 110 be made in the thyroid cartilage 108. FIG. 17 shows the thyroplasty implant 200 in place, thus allowing for a combined medialization thyroplasty-arytenoid adduction procedure.

Figure 19:
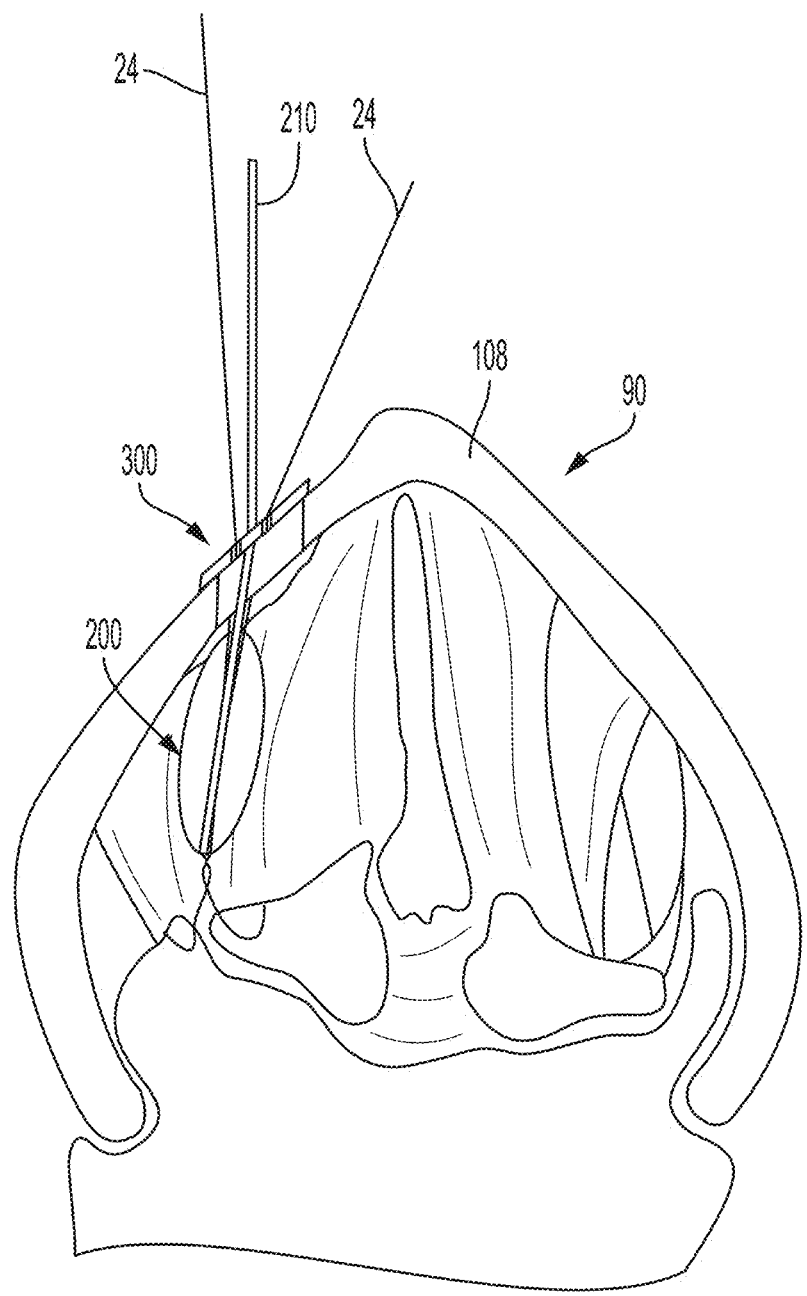
FIG. 19 is a schematic superior view of the larynx, where one embodiment of the suture wire complex of the present invention has been used to rotate the arytenoid of the paralyzed vocal fold and a thyroplasty implant has been passed along one of the suture strands to provide bulk to the vocal fold and a reconstruction device has secured the timplant and repaired the incision damage to the thyroid cartilage.

FIGS. 18-20 shows the procedure being finished. A reconstruction device 300 reconstructing the small defect 110 in the thyroid cartilage 108 is passed down the suture strands 24. This fills the defect 100 created during the procedure and also serves to provide additional support to the sutures 24. The sutures 24 from the suture wire complex and the thyroplasty sutures 210, are tied off 400 to secure the sutures, and secure the positioning the arytenoid 106 and the thyroplasty implant 200.

In another embodiment, an expanding thyroplasty implant 220 can be used (see FIG. 21). In this embodiment the suture wire complex 20 of the present invention has been used to rotate the arytenoid 106 ipsilateral to the paralyzed vocal fold 102 and the expanding thyroplasty implant 220 has been passed along one of the suture strands 24 to provide bulk to the vocal fold 100, thus allowing for a combined medialization thyroplasty-arytenoid adduction procedure.

In yet another embodiment, an inflatable thyoplasty implant can be used 222 (see FIG. 22). In this embodiment the suture wire complex 20 of the present invention has been used to rotate the arytenoid 106 ipsilateral to the paralyzed vocal fold 102 and the inflatable thyroplasty implant 222 has been passed along one of the suture strands 24 to provide bulk to the vocal fold 100, thus allowing for a combined medialization thyroplasty-arytenoid adduction procedure.

Figure 23:
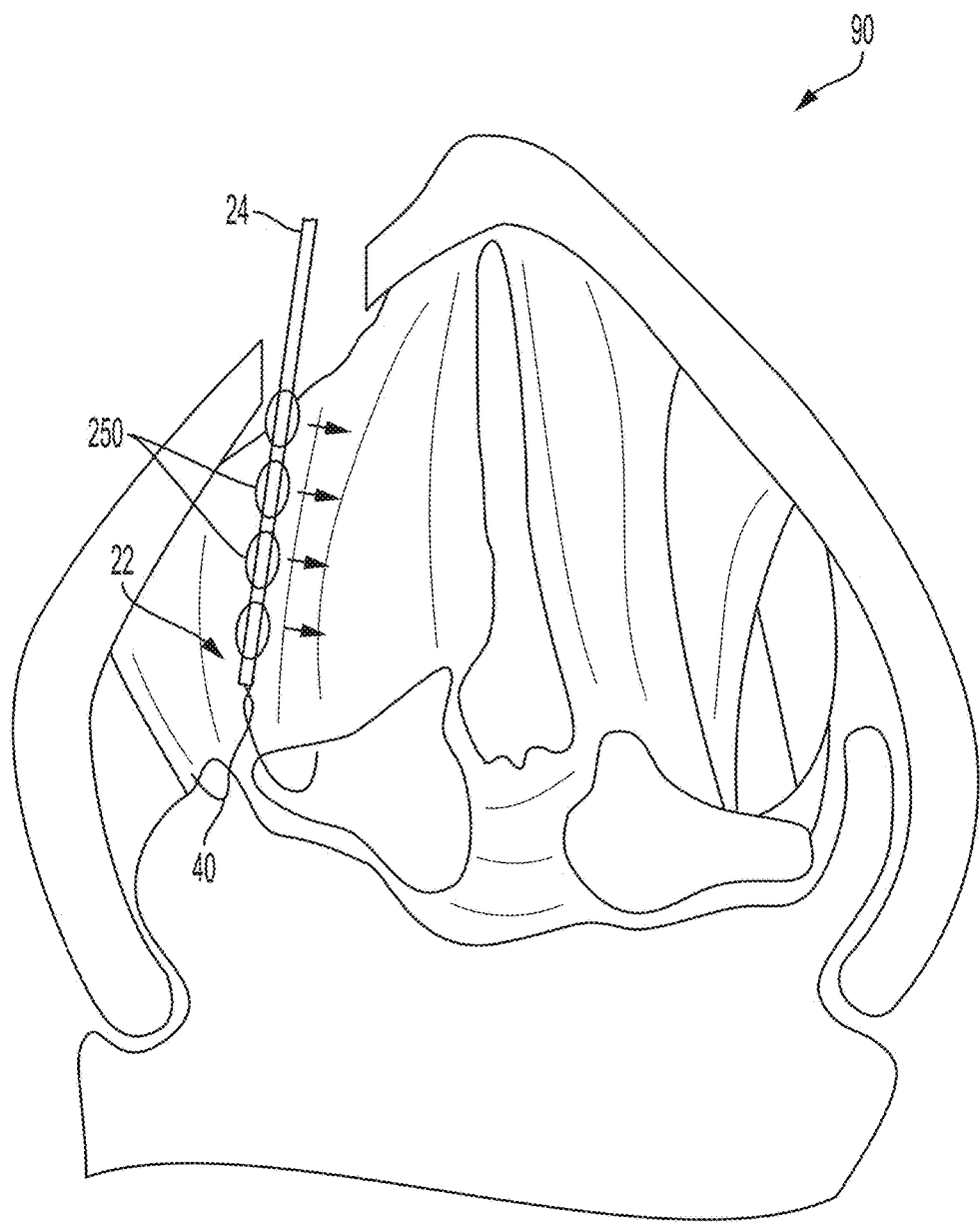
FIG. 23 is a schematic superior view of the larynx, where an embodiment of the suture wire complex of the present invention has been used to stabilize the arytenoid of the affected vocal fold and drug delivery beads has been passed along one of the suture strands to allow for them to disperse the drugs contained within the beads to the targeted area.

In another aspect, the device 10 described herein may be used as a scaffold or delivery mechanism for biochemical or therapeutic purposes, as shown in FIG. 23. The device 10 can be inserted via a simple, minimally invasive procedure, as described above. Once in place within the muscle of the vocal fold 100, the device 10 can be used as a scaffold for stability or provide a therapeutic corridor through which compositions may be delivered. Compositions may include an implant, as detailed above, or compositions comprising an agent, such as a pharmaceutical compound, growth medium or factors, cytokine, hormones, polypeptide, polynucleotide, stem cells, chemotherapeutic, radiation therapy (e.g., one with no external beam), or other agents known in the art. In some embodiments, the device may be used for brachytherapy by delivering of radiation therapy. The composition may be in any suitable form, such as, for example, beads, resin, solution, gel, nanoparticles, or emulsions. The composition may include drug delivery beads 250. Similar beads 250 may be used to deliver radiation therapy. For example, chemotherapeutic drugs could be delivered locally via a time-released mechanism for patients with cancer of the vocal fold 100. As another example, steroids could be delivered to patients with acute or chronic laryngitis to decrease inflammation. In other embodiments, stem cells could be delivered to repopulate and restore the normal properties of the lamina propria in patients with vocal fold scar. In patients with presbylaryngis or other disorders characterized by muscular atrophy, growth factors could be delivered to promote local muscular restoration.

In another aspect, provided is a volume measuring device 275 to measure the volume necessary to medialize a vocal fold and close a glottal gap 104 (see FIG. 24). An implant, as detailed above, of the same volume may then be administered to medialize the vocal fold and close the glottal gap. A device 10 as described herein may be used in combination with a balloon 280 and a syringe 278. The volume measuring device 275 includes a void measuring balloon 280 attached to a calibrated syringe 278. A suture wire complex 20 as detailed above may be advanced from the subject's anterior arytenoid to the muscular process 112 of the larynx 90. The balloon 280 of the volume measuring device 275 can be passed along the suture 24 to the muscular process 112. The balloon 280 is inflated with air or fluid and presses against the muscular process 112 and arytenoid 106, medializing the vocal fold and closing the glottal gap 104. The volume of the volume measuring balloon 280 may be determined by the syringe 278. The volume necessary to medialize the vocal fold 100 may be determined by correlating it with the volume of the inflated void measuring balloon 280. The void measuring balloon 280 can then be deflated and removed, and a permanent implant with the specified volume could be inserted, as detailed above.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including but not limited to") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims.

EXAMPLES

Example 1: Materials and Methods

Larynges

Four larynges were excised postmortem from canines sacrificed for non-research purposes according to the protocol described by Jiang and Titze. (Jiang J J, Titze I R. Laryngoscope 1993, 103, 872-82, incorporated herein by reference). As the properties of the canine and human larynx are similar, it is an appropriate model for studying human laryngeal physiology. Larynges were examined for evidence of trauma or disorders; any larynges exhibiting trauma or disorders were excluded. Following visual inspection, larynges were frozen in 0.9% saline solution.

Apparatus

Prior to the experiment, the epiglottis, corniculate cartilages, cuneiform cartilages, and ventricular folds were dissected away to expose the true vocal folds. The superior cornu and posterosuperior part of the thyroid cartilage ipsilateral to the normal vocal fold were also dissected away to facilitate insertion of a lateral 3-pronged micrometer into the arytenoid cartilage 106. The larynx was mounted on the apparatus as specified by Jiang and Titze (Jiang J J, Titze I R. Laryngoscope 1993, 103, 872-82, incorporated herein by reference). A metal pull clamp was used to stabilize the trachea to a tube connected to a pseudolung which served as a constant pressure source. Insertion of one 3-pronged micrometer in the arytenoid cartilage ipsilateral to the dissected thyroid cartilage allowed for adduction of one vocal fold, simulating unilateral VFP in the unadducted vocal fold as in Czerwonka et al. (Czerwonka L, Ford C N, Machi A T, et al. Laryngoscope 2009, 119, 591-6, incorporated herein by reference). An additional 3-pronged micrometer was placed against the contralateral thyroid lamina for stability without providing vocal fold adduction. Methodological consistency was maintained by always adducting the contralateral arytenoid (simulated normal) to the midline. Micrometer positioning remained constant across sets of trials within the same larynx. Tension on the vocal folds and control of vocal fold elongation was accomplished by attaching the superior anteromedial thyroid cartilage, just inferior to the thyroid notch, to an anterior micrometer. Vocal fold elongation and adduction remained constant for all trials.

The pseudolung used to initiate and sustain phonation in these trials was designed to simulate the human respiratory system. Pressurized airflow was passed through two Concha Therm III humidifiers (Fisher & Paykel Healthcare Inc., Laguna Hills, Calif.) in series to humidify and warm the air. The potential for dehydration was further decreased by frequent application of 0.9% saline solution between trials. Airflow was controlled manually and was measured using an Omega airflow meter (model FMA-1601A, Omega Engineering Inc., Stamford, Conn.). Pressure measurements were taken immediately before the air passed into the larynx using a Heise digital pressure meter (901 series, Ashcroft Inc., Stratford, Conn.).

Acoustic data were collected using a dbx microphone (model RTA-M, dbx Professional Products, Sandy, Utah) positioned at a 45° angle to the vocal folds. The microphone was placed 10 cm from the glottis to minimize acoustic noise produced by turbulent airflow. Acoustic signals were subsequently amplified by a Symetrix preamplifier (model 302, Symetrix Inc., Mountlake Terrace, Wash.). A National Instruments data acquisition board (model AT-MIO-16; National Instruments Corp, Austin, Tex.) and customized LabVIEW 8.5 software were used to record airflow, pressure, and acoustic signals on a personal computer. Aerodynamic data were recorded at a sampling rate of 100 Hz and acoustic data at 40,000 Hz. Experiments were conducted in a triple-walled, sound-attenuated room to reduce background noise and stabilize humidity levels and temperature.

Experimental Methods

Trials were conducted as a sequence of 5 second periods of phonation, followed by 5 second periods of rest. Five trials were performed for each condition. During each trial, airflow passing through the larynx was increased gradually and consistently until the onset of phonation. Larynges were thoroughly hydrated with saline solution between trials and between sets of trials to eliminate any potentially confounding effects of dehydration.

ML was performed using a Silastic implant (Dow Corning Corporation, Midland, Mich.). The implant was inserted through a 6×11 mm thyroplasty window in the thyroid cartilage 108 ipsilateral to the paralyzed vocal fold. Traditional AA was performed after a set of trials was conducted analyzing the effect of ML. The procedure was performed according to the clinical descriptions by Isshiki (Isshiki N, Tanabe M, Sawada M. Arch. Otolaryngol. 1978, 104, 555-558, incorporated herein by reference). One suture was passed with a needle from the muscular process of the arytenoid anteriorly through the paraglottic space through the thyroid cartilage just lateral to the anterior commissure and the second inferior to the cartilage was tightened to rotate the arytenoid 106 and adduct the simulated paralyzed fold. The optimal degree of rotation was determined using real-time measurements of VE (Hoffman M R, Surender K, Chapin W J, et al. Laryngoscope 2011, 121, 339-345, incorporated herein by reference). Images demonstrating vocal fold position for the normal, vocal fold paralysis, traditional AA, and anterior AA trials are provided in FIG. 1. The anterior approach is described in detail below.

Anterior Approach to Arytenoid Adduction

Figure 2:
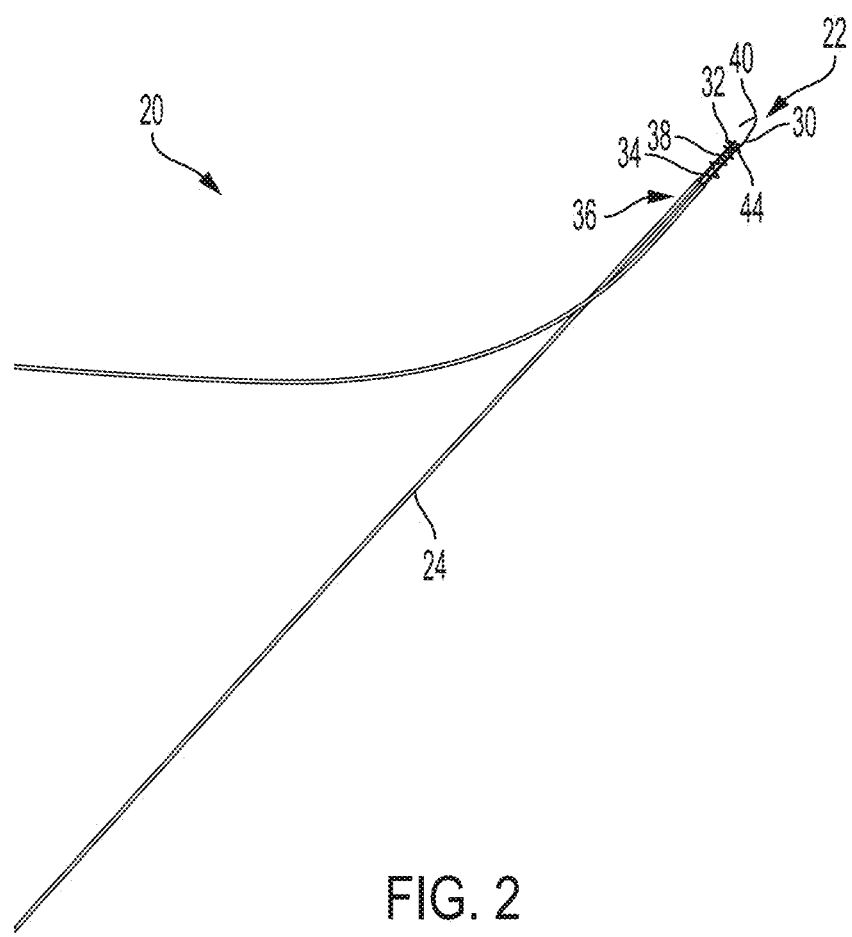
FIG. 2 is a schematic diagram of a suture wire complex of the present invention.

Stainless steel wire with diameter of 0.015" and length of approximately 5 cm was curled around a gauge needle. A hook was formed at one end of the wire by bending it approximately 2 mm from the end. The specific dimensions of the hook are not critical and the length can easily be decreased once placed inside the larynx if necessary. Gore-Tex suture 24 was threaded through the curled wire and doubled back outside the curled portion proximal to the hook (FIG. 2). In this experiment, CV-2 expanded polytetrafluoroethylene (Gore-Tex) suture was used, though the particular size is not important and can be varied across cases. Once the suture wire complex is created, it is threaded through a 14-gauge needle. A 20-gauge needle serving as a guide needle is also threaded through the 14-gauge needle (FIG. 3). When performing the procedure, the guide needle and thus suture wire complex can be passed either through the thyroplasty window or through the cricothyroid membrane. The guide needle is passed first and advanced to the muscular process of the arytenoid. Once the muscular process is reached and confirmed by visualization of arytenoid movement with manipulation of the guide needle, the 14-gauge needle containing the suture wire complex is passed over the guide needle. When the muscular process is reached, the suture wire complex is pushed outside the 14-gauge needle. The 14-gauge needle can then be removed. Verification that the suture wire complex has been secured on the tissue surrounding the muscular process is made prior to removing the guide needle. After removal of the guide needle, optimal degree of medialization is obtained by tightening the suture; the two ends are then tied external to the larynx and secured.

Data Analysis

Airflow and pressure at the phonation onset were recorded as the phonation threshold flow (PTF) and phonation threshold pressure (PTP), respectively. Phonation threshold power (PTW) is the product of these values. PTF, PTP, and PTW were determined manually using customized LabVIEW 8.5 software.

Measured acoustic parameters included fundamental frequency (FO), signal-to-noise ratio (SNR), percent jitter, and percent shimmer. Acoustic signals were trimmed using GoldWave 5.1.2600.0 (GoldWave Inc., St. John's, Canada) and analyzed using TF32 software (Madison, Wis.).

Statistical Analysis

Paired t-tests were performed to determine: 1) if anterior AA led to improved voice quality compared to simulated VFP; 2) if anterior AA produced the same degree of improvement in voice quality compared to traditional AA; and 3) if anterior AA restored normal voice, as demonstrated by comparisons to simulated normal. If data did not meet assumptions for parametric testing, Wlcoxon-Mann-Whitney rank sum tests were performed. All tests were two-tailed with a significance level of $\alpha=0.05$.

Example 2: Anterior Arytenoid Adduction

Four larynges were excised and prepared as described in Example 1. The arytenoid was adducted from the anterior as described in Example 1. Briefly, Stainless steel wire with diameter of 0.015" and length of approximately 5 cm was curled around a 20 gauge needle. A hook was formed at one end of the wire by bending it approximately 2 mm from the end. The specific dimensions of the hook are not critical and the length can easily be decreased once placed inside the larynx if necessary. Gore-Tex suture was threaded through the curled wire and doubled back outside the curled portion proximal to the hook (FIG. 2). In this experiment, CV-2 expanded polytetrafluoroethylene (Gore-Tex) suture was used, though the particular size is not important and can be varied across cases. Once the suture wire complex is created, it is threaded through a 14-gauge needle. A 20-gauge needle serving as a guide needle is also threaded through the 14-gauge needle (FIG. 3). When performing the procedure, the guide needle and thus suture wire complex 20 can be passed either through the thyroplasty window or through the cricothyroid membrane. The guide needle is passed first and advanced to the muscular process of the arytenoid. Once the muscular process is reached and confirmed by visualization of arytenoid movement with manipulation of the guide needle, the 14-gauge needle containing the suture wire complex is passed over the guide needle. When the muscular process is reached, the suture wire complex is pushed outside the 14-gauge needle. The 14-gauge needle can then be removed. Verification that the suture wire complex has been secured on the tissue surrounding the muscular process is made prior to removing the guide needle. After removal of the guide needle, optimal degree of medialization is obtained by tightening the suture; the two ends are then tied external to the larynx and secured. Results were compared to vocal fold paralysis (VFP), as detailed below.

Aerodynamics

Compared to VFP, anterior AA led to significantly lower PTP ($p=0.045$), PTF ($p=0.006$), and PTW ($p=0.003$). Aerodynamic parameters for anterior AA did not differ significantly compared to those obtained for either normal or traditional AA (Table 1; Table 3).

TABLE 1

Summary aerodynamic data presented as mean ± standard deviation (n = 4). A significance level of $\alpha = 0.05$ was used for all tests.

| Parameter | Normal | VFP | ML | Traditional AA | Anterior AA |
|---|---|---|---|---|---|
| PTP | 19.96 ± 11.77 | 22.58 ± 4.03 | 19.65 ± 2.62 | 19.65 ± 21.13 | 13.68 ± 6.38 |
| PTF | 30 ± 11 | 106 ± 22 | 82 ± 17 | 47 ± 32 | 36 ± 21 |
| PTW | 693 ± 568 | 2414 ± 735 | 1614 ± 391 | 972 ± 1091 | 589 ± 616 |

PTF = phonation threshold flow (L/min);
PTP = phonation threshold pressure (cmH2O);
PTW = phonation threshold power (L/min * cmH2O);
VE = vocal efficiency (units);
VFP = vocal fold paralysis;
ML = medialization laryngoplasty;
AA = arytenoid adduction.
Values are presented as mean ± standard deviation.

Acoustics

Compared to VFP, anterior AA led to significant decreases in percent jitter ($p=0.028$) and percent shimmer ($p=0.001$) and a significant increase in SNR ($p=0.034$). FO was not significantly affected ($p=0.250$). Acoustic parameters for anterior AA did not differ significantly compared to those obtained for either normal or traditional AA (Table 2; Table 3); however, the difference in FO between traditional AA and anterior AA approached significance ($p=0.094$).

TABLE 2

Summary acoustic data presented as mean ± standard deviation (n = 4).
A significance level of α = 0.05 was used for all tests.

| Parameter | Normal | VFP | ML | Traditional AA | Anterior AA |
|---|---|---|---|---|---|
| $F_0$ | 390 ± 127 | 213 ± 48 | 220 ± 52 | 168 ± 47 | 285 ± 62 |
| % Jitter | 1.52 ± 1.15 | 5.33 ± 2.73 | 3.03 ± 0.53 | 1.49 ± 0.54 | 1.74 ± 0.98 |
| % Shimmer | 8.88 ± 6.29 | 28.75 ± 10.48 | 18.91 ± 4.30 | 5.58 ± 1.42 | 11.77 ± 9.03 |
| SNR | 17.37 ± 11.02 | 4.04 ± 3.49 | 5.65 ± 2.40 | 14.56 ± 3.85 | 14.40 ± 8.44 |

SNR = signal-to-noise ratio;
F0 = fundamental frequency;
VFP = vocal fold paralysis;
ML = medialization laryngoplasty;
AA = arytenoid adduction.
Values are presented as mean ± standard deviation.

TABLE 3

P-values obtained from paired t-tests comparing the aerodynamic and acoustic outcomes obtained using anterior arytenoid adduction to those obtained from the other conditions.

| Parameter | Normal | VFP | ML | Traditional AA |
|---|---|---|---|---|
| PTP | 0.150 | 0.045 | 0.072 | 1.000 |
| PTF | 0.498 | 0.006 | <0.001 | 0.410 |
| PTW | 0.620 | 0.003 | 0.001 | 0.256 |
| $F_0$ | 0.340 | 0.250 | 0.303 | 0.094 |
| % Jitter | 0.340 | 0.028 | 0.079 | 0.616 |
| % Shimmer | 0.748 | 0.001 | 0.253 | 0.281 |
| SNR | 0.357 | 0.034 | 0.083 | 0.970 |

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

We claim:

1. A device for arytenoid adduction comprising a suture wire complex comprising a wire hook complex connected to a suture, wherein the wire hook complex comprises a wire having a first end and a second end at opposite ends of a longitudinal axis, the wire forming a spiral along the longitudinal axis and having a hook at the first end; and the suture threaded through the spiral of the wire from the second end to the first end.

2. The device of claim 1, wherein the suture forms a turn at the first end and passes exterior to the spiral to the second end.

3. The device of claim 2, further comprising a first needle enclosing the suture wire complex.

4. The device of claim 3, further comprising a second needle enclosed by the first needle.

5. The device of claim 4, further comprising a localizing trocar for enclosing the first needle.

6. A method of delivering a composition to a vocal fold of a subject in need thereof, the subject having a larynx having anterior thyroid cartilage, an arytenoid with a muscular process, vocal folds, and a glottal gap between the vocal folds, the method comprising:
   providing a suture wire complex comprising a wire hook complex connected to a suture, the wire hook complex comprising a wire having a first end and a second end at opposite ends of a longitudinal axis, the wire forming a spiral along the longitudinal axis and having a hook at the first end, and a suture threaded through the spiral of the wire from the second end to the first end, the suture forming a turn at the first end and passing exterior to the spiral to the second end;
   advancing the suture wire complex from the subject's anterior thyroid cartilage to one of the vocal folds; and
   advancing the composition from the subject's anterior thyroid cartilage to the vocal fold along the longitudinal axis of the wire hook complex.

7. The method of claim 6, wherein the composition comprises at least one of a pharmaceutical compound, polypeptide, polynucleotide, cytokine, hormone, and stem cell.

8. The method of claim 6, wherein a first needle encloses the suture wire complex.

9. The method of claim 8, wherein a localizing trocar encloses the first needle.

10. A method of determining the volume required to medialize a vocal fold and close a glottal gap in the larynx of a subject, the subject having a larynx having anterior thyroid cartilage, an arytenoid with a muscular process, soft tissue surrounding the muscular process, vocal folds, and a glottal gap between the vocal folds, the method comprising:
   providing a suture wire complex comprising a wire hook complex connected to a suture, the wire hook complex comprising a wire having a first end and a second end at opposite ends of a longitudinal axis, the wire forming a spiral along the longitudinal axis and having a hook at the first end, and a suture threaded through the spiral of the wire from the second end to the first end, the suture forming a turn at the first end and passing exterior to the spiral to the second end;
   providing a volume measuring device comprising a syringe and a volume measuring balloon;
   advancing the suture wire complex from the subject's anterior thyroid cartilage to the muscular process of the subject's larynx;
   advancing the balloon along the longitudinal axis of the suture wire complex to the muscular process;
   inflating the balloon to pressure the muscular process to medialize the vocal fold and close the glottal gap;
   determining the volume of the filled balloon using the calibrated syringe; and
   determining the volume required to medialize the vocal fold and close the glottal gap, wherein the volume required is equal to the volume of the filled balloon.

* * * * *